(12) United States Patent
Mirigian et al.

(10) Patent No.: US 9,282,971 B2
(45) Date of Patent: Mar. 15, 2016

(54) IMPLANTS, METHODS OF MANUFACTURING THE SAME, AND DEVICES AND METHODS FOR DELIVERING THE IMPLANTS TO A VASCULAR DISORDER OF A PATIENT

(71) Applicant: INCUMEDx, Inc., Fremont, CA (US)

(72) Inventors: Gregory Edwin Mirigian, Dublin, CA (US); Be Thi Le, San Jose, CA (US); Regina Coeli Velasco, Fremont, CA (US)

(73) Assignee: INCUMEDx, Inc., Fremont, CA (US)

(*) Notice: Subject to any disclaimer, the term of this patent is extended or adjusted under 35 U.S.C. 154(b) by 127 days.

(21) Appl. No.: 14/196,253

(22) Filed: Mar. 4, 2014

(65) Prior Publication Data

US 2014/0277085 A1    Sep. 18, 2014

Related U.S. Application Data

(60) Provisional application No. 61/869,265, filed on Aug. 23, 2013, provisional application No. 61/782,940, filed on Mar. 14, 2013.

(51) Int. Cl.
*A61M 29/00* (2006.01)
*A61B 17/12* (2006.01)
*A61B 17/04* (2006.01)

(52) U.S. Cl.
CPC ....... *A61B 17/12113* (2013.01); *A61B 17/0467* (2013.01); *A61B 17/1214* (2013.01);
(Continued)

(58) Field of Classification Search
CPC .................. A61B 17/12113; A61B 17/12145; A61B 2017/12054; A61B 17/1214; A61B 17/12154

USPC .................................. 606/191, 200; 623/1.11
See application file for complete search history.

(56) References Cited

U.S. PATENT DOCUMENTS 5,250,071 A    10/1993   Palermo
5,261,916 A    11/1993   Engelson
(Continued)

FOREIGN PATENT DOCUMENTS

EP    1010396 A1    6/2000
EP    1621149 A1    2/2006
(Continued)

OTHER PUBLICATIONS

International Search Report and Written Opinion for International Application No. PCT/US2014/020157, mailed Sep. 30, 2014, 17 pages.

(Continued)

*Primary Examiner* — Katherine M Shi
(74) *Attorney, Agent, or Firm* — Goodwin Procter LLP

(57) ABSTRACT

A device for delivering an implant to a vascular disorder of a patient includes a delivery pusher. A stationary blade may be coupled to the delivery pusher. The stationary blade may include a sharp and stationary cutting component for cutting through a suture coupling the implant to the delivery pusher and for thereby releasing the implant when placed in proximity to the vascular disorder. In some cases, the strength of a junction connecting the suture to the implant is equal to or greater than the tensile strength of the suture itself. Additionally, or alternatively, a detachment handle may be fixedly and permanently attached to the delivery pusher such that a user of the device need not couple the detachment handle to the delivery pusher. The detachment handle may include a user manipulable component for initiating a mechanical release of the implant when placed in proximity to the vascular disorder.

24 Claims, 23 Drawing Sheets

(52) U.S. Cl.
CPC .............. *A61B2017/1205* (2013.01); *A61B 2017/12054* (2013.01); *A61B 2017/12095* (2013.01); *Y10T 29/49826* (2015.01)

(56) References Cited

U.S. PATENT DOCUMENTS

| | | | |
|---|---|---|---|
| 5,263,964 A | 11/1993 | Purdy | |
| 5,290,230 A | 3/1994 | Ainsworth et al. | |
| 5,304,195 A | 4/1994 | Twyford, Jr. et al. | |
| 5,312,415 A | 5/1994 | Palermo | |
| 5,350,397 A | 9/1994 | Palermo et al. | |
| 5,451,209 A | 9/1995 | Ainsworth et al. | |
| 5,582,619 A | 12/1996 | Ken | |
| 5,690,667 A | 11/1997 | Gia | |
| 5,725,546 A | 3/1998 | Samson | |
| 5,792,154 A | 8/1998 | Doan et al. | |
| 5,797,928 A | 8/1998 | Kogasaka | |
| 5,814,062 A | 9/1998 | Sepetka et al. | |
| 5,833,705 A | 11/1998 | Ken et al. | |
| 5,853,418 A | 12/1998 | Ken et al. | |
| 5,868,754 A | 2/1999 | Levine et al. | |
| 5,911,737 A | 6/1999 | Lee et al. | |
| 5,944,733 A | 8/1999 | Engelson | |
| 6,004,338 A | 12/1999 | Ken et al. | |
| 6,013,084 A | 1/2000 | Ken et al. | |
| 6,022,369 A | 2/2000 | Jacobsen et al. | |
| 6,068,644 A | 5/2000 | Lulo et al. | |
| 6,193,728 B1 | 2/2001 | Ken et al. | |
| 6,221,066 B1 | 4/2001 | Ferrera et al. | |
| 6,238,415 B1 | 5/2001 | Sepetka et al. | |
| 6,280,457 B1 | 8/2001 | Wallace et al. | |
| 6,296,622 B1 | 10/2001 | Kurz et al. | |
| 6,478,773 B1 | 11/2002 | Gandhi et al. | |
| 6,551,305 B2 | 4/2003 | Ferrera et al. | |
| 6,562,021 B1 | 5/2003 | Derbin et al. | |
| 6,835,185 B2 | 12/2004 | Ramzipoor et al. | |
| 6,887,235 B2 | 5/2005 | O'Connor et al. | |
| 6,966,892 B2 | 11/2005 | Gandhi et al. | |
| 7,137,990 B2 | 11/2006 | Hebert et al. | |
| 7,166,122 B2 | 1/2007 | Aganon et al. | |
| 7,198,613 B2 | 4/2007 | Gandhi et al. | |
| 7,255,707 B2 | 8/2007 | Ramzipoor et al. | |
| 7,377,932 B2 | 5/2008 | Mitelberg et al. | |
| 7,422,569 B2 | 9/2008 | Wilson et al. | |
| 7,485,122 B2 | 2/2009 | Teoh | |
| 7,608,089 B2 | 10/2009 | Wallace et al. | |
| 7,695,484 B2 | 4/2010 | Wallace et al. | |
| 7,722,636 B2 | 5/2010 | Farnan | |
| 7,901,444 B2 | 3/2011 | Slazas | |
| 7,938,845 B2 | 5/2011 | Aganon et al. | |
| 7,942,894 B2 | 5/2011 | West | |
| 7,972,342 B2 | 7/2011 | Gandhi et al. | |
| 7,985,238 B2 | 7/2011 | Balgobin et al. | |
| 8,062,325 B2 | 11/2011 | Mitelberg et al. | |
| 8,328,860 B2 | 12/2012 | Strauss et al. | |
| 8,333,796 B2 | 12/2012 | Tompkins et al. | |
| 8,597,323 B1 | 12/2013 | Plaza et al. | |
| 8,777,978 B2 | 7/2014 | Strauss et al. | |
| 8,795,316 B2 | 8/2014 | Balgobin et al. | |
| 8,940,011 B2 | 1/2015 | Teoh et al. | |
| 8,945,171 B2 | 2/2015 | Lim | |
| 2002/0002382 A1 | 1/2002 | Wallace et al. | |
| 2002/0165569 A1 | 11/2002 | Ramzipoor et al. | |
| 2004/0002732 A1 | 1/2004 | Teoh et al. | |
| 2005/0149108 A1 | 7/2005 | Cox | |
| 2006/0025802 A1 | 2/2006 | Sowers | |
| 2006/0116714 A1 | 6/2006 | Sepetka et al. | |
| 2007/0005081 A1 | 1/2007 | Findlay et al. | |
| 2009/0270901 A1 | 10/2009 | Kelleher et al. | |
| 2009/0297582 A1 | 12/2009 | Meyer et al. | |
| 2010/0121350 A1 | 5/2010 | Mirigian | |
| 2010/0268201 A1 | 10/2010 | Tieu et al. | |
| 2011/0092997 A1 | 4/2011 | Kang | |
| 2011/0213406 A1 | 9/2011 | Aganon et al. | |
| 2013/0261657 A1 | 10/2013 | Lorenzo | |
| 2013/0325054 A1 | 12/2013 | Watson | |
| 2014/0058434 A1 | 2/2014 | Jones et al. | |
| 2014/0058435 A1 | 2/2014 | Jones et al. | |
| 2014/0277078 A1 | 9/2014 | Slazas et al. | |
| 2014/0277085 A1 | 9/2014 | Mirigian et al. | |

FOREIGN PATENT DOCUMENTS

| | | |
|---|---|---|
| EP | 1806106 A2 | 7/2007 |
| EP | 2777545 A2 | 9/2014 |
| WO | WO-9406503 A1 | 3/1994 |
| WO | WO-2013081227 A1 | 6/2013 |

OTHER PUBLICATIONS

Invitation to Pay Additional Fees and, Where Applicable, Protest Fee for PCT/US2014/020157, Mailed Jul. 2, 2014, 7 pages.

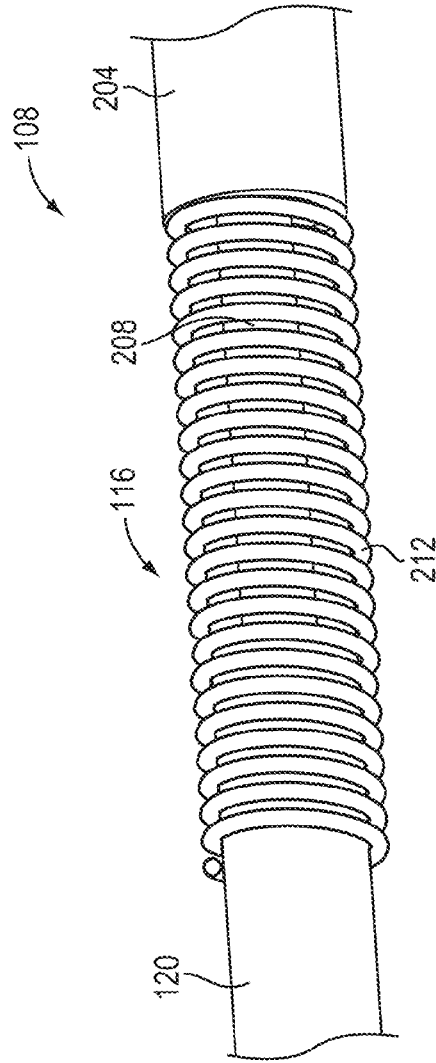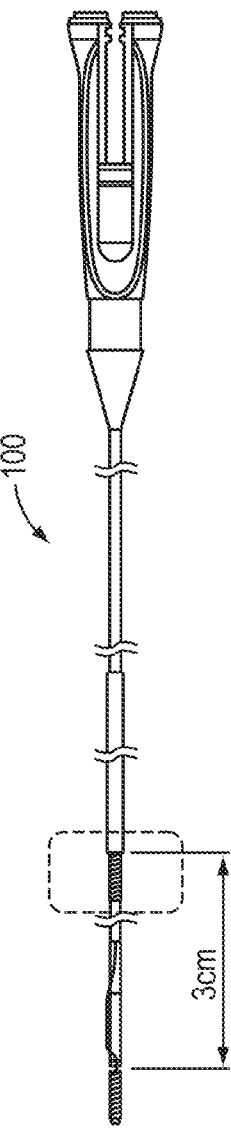
FIG. 2

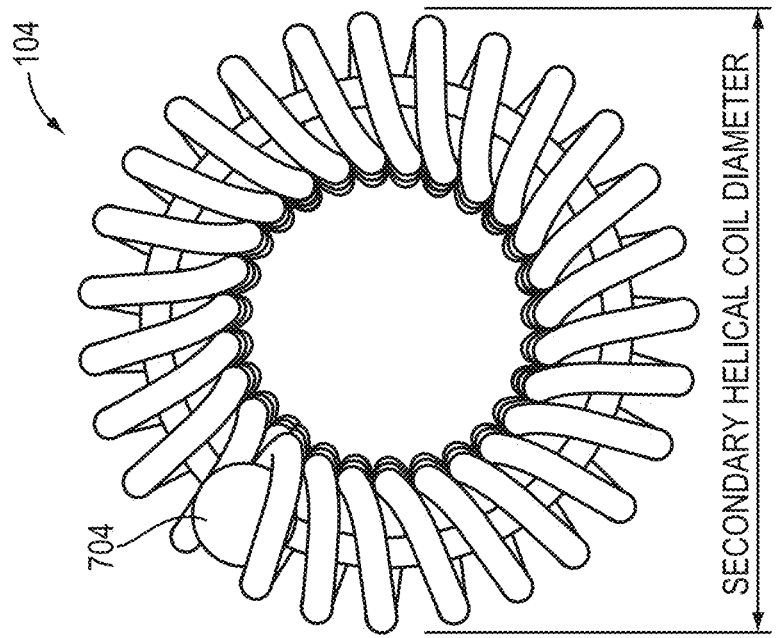
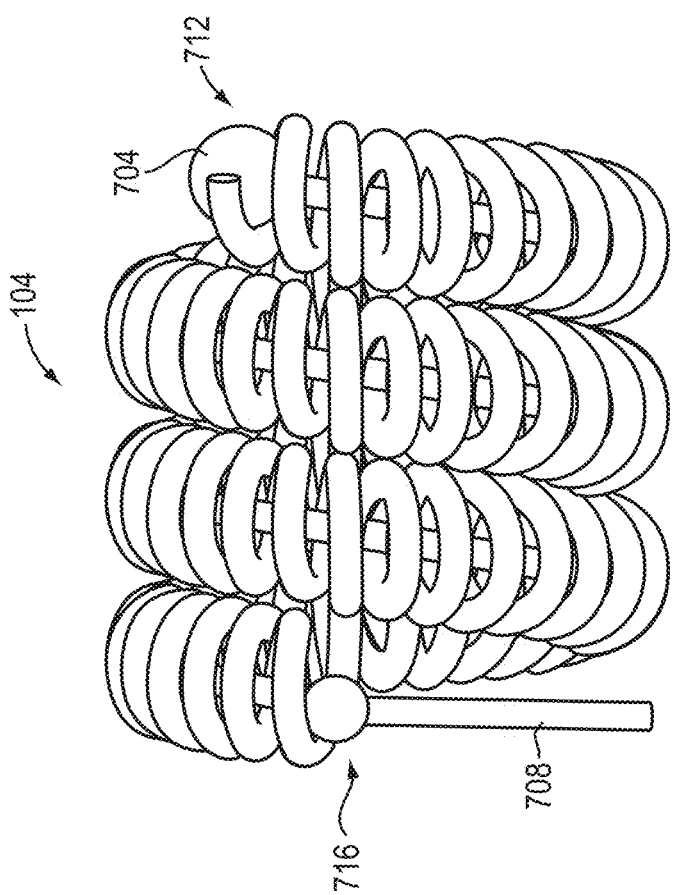

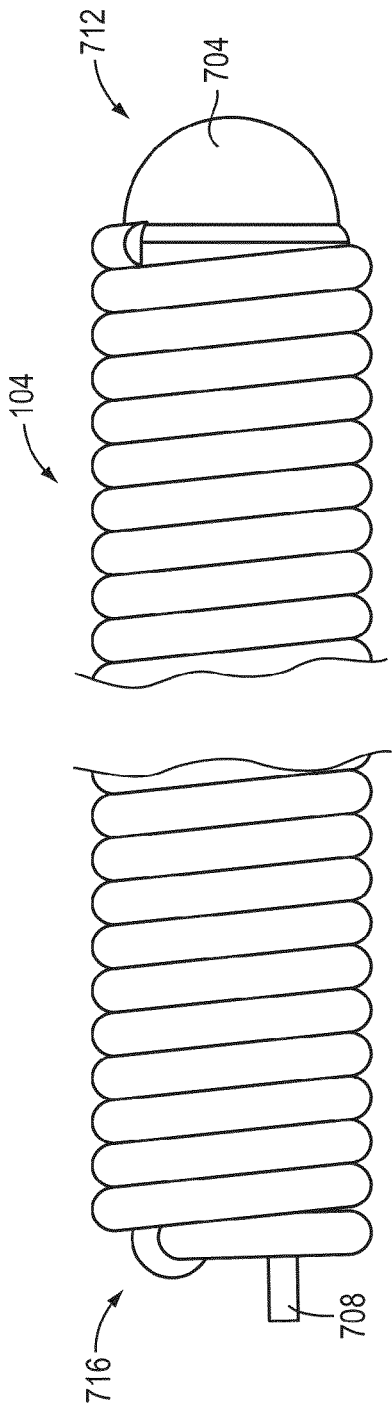
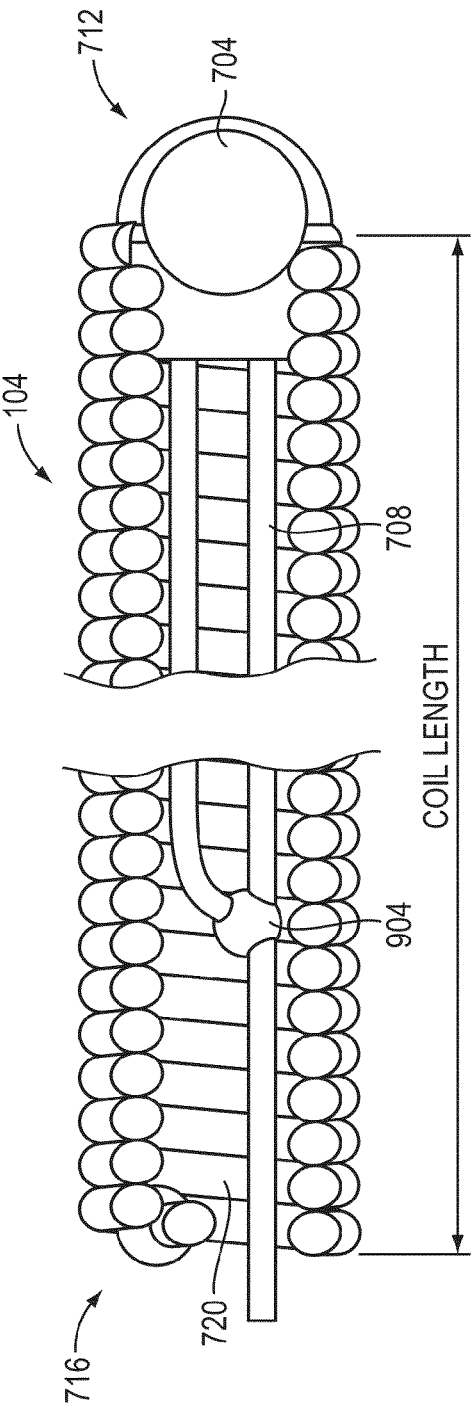
FIG. 9A
FIG. 9B

BLADE V-SCYTHE

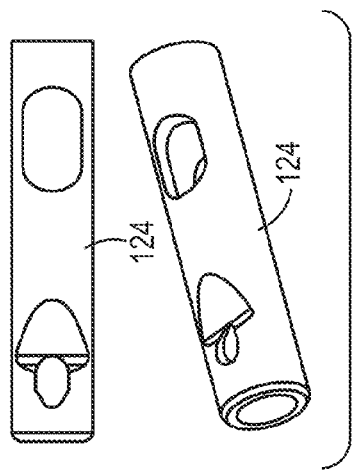
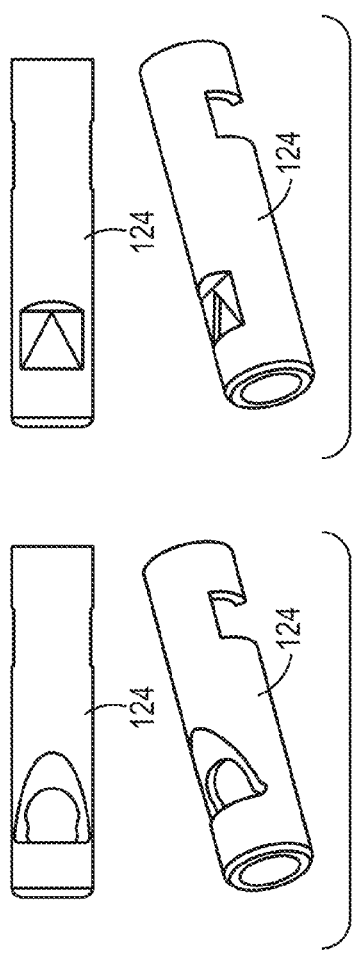
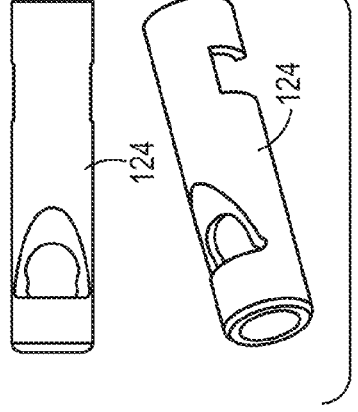
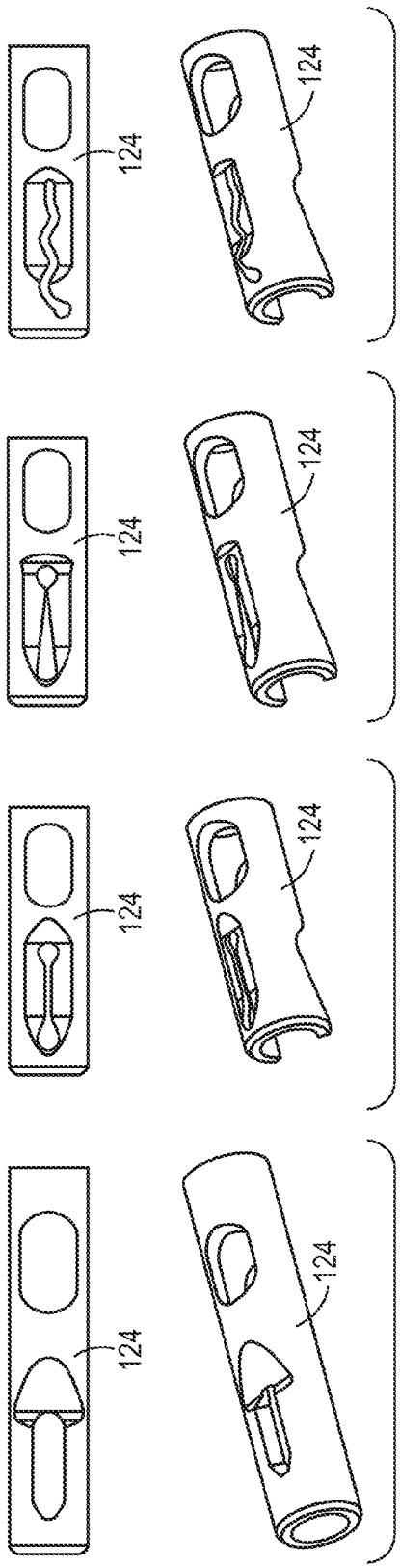
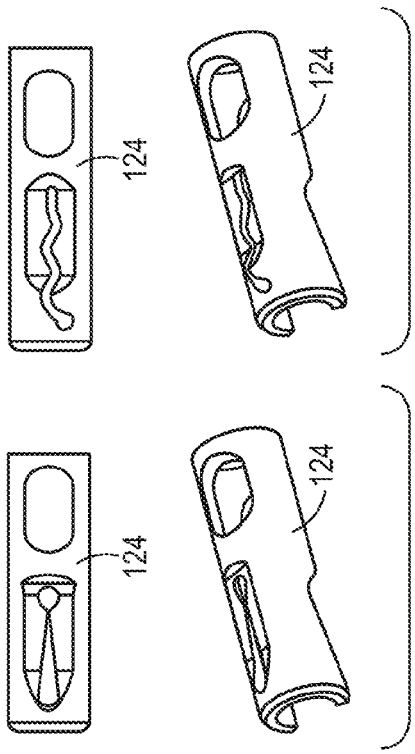
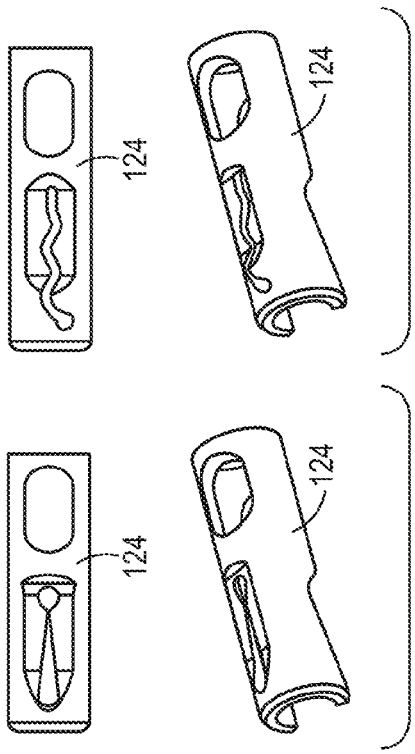
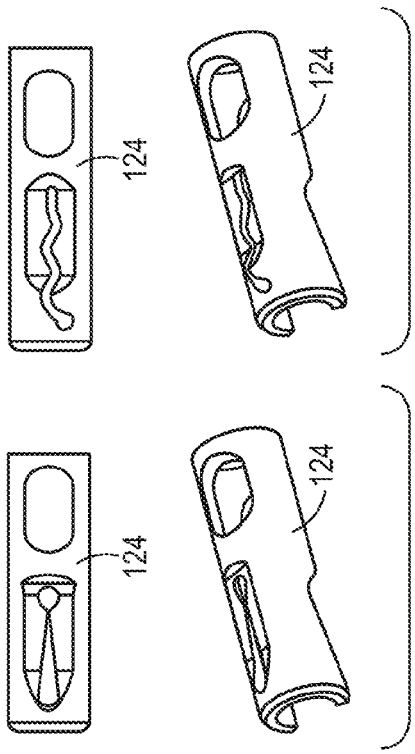

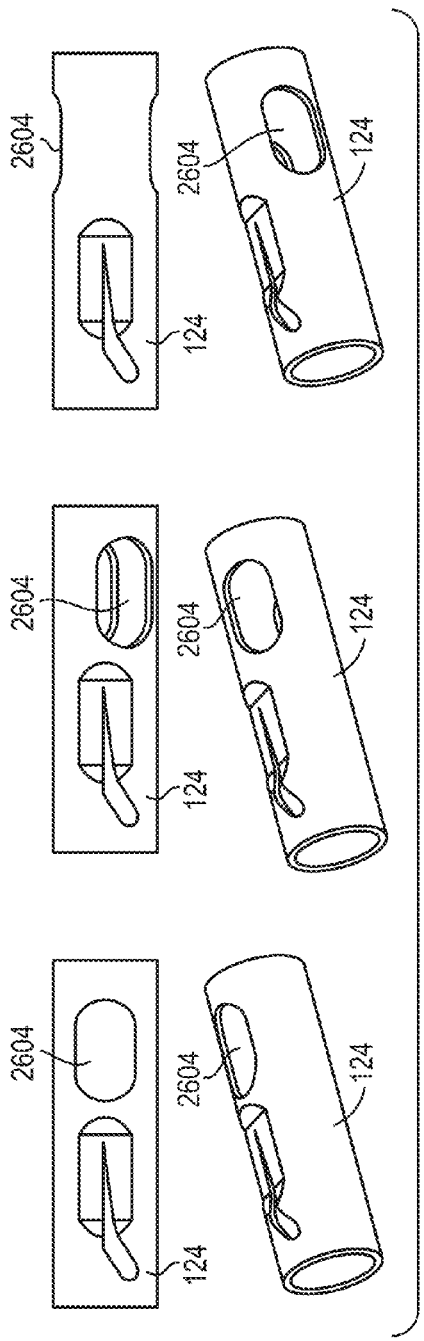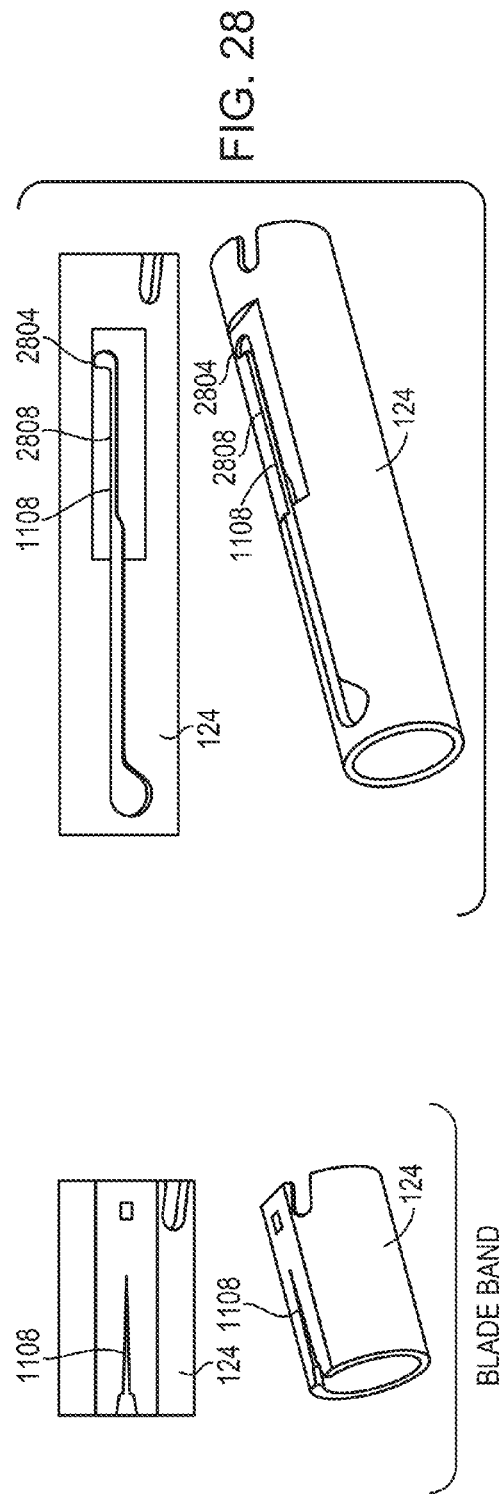

ated on Mar. 14, 2013, and U.S. Provisional Patent Application
IMPLANTS, METHODS OF MANUFACTURING THE SAME, AND DEVICES AND METHODS FOR DELIVERING THE IMPLANTS TO A VASCULAR DISORDER OF A PATIENT

CROSS-REFERENCE TO RELATED APPLICATIONS

This application claims priority to and the benefit of, and incorporates herein by reference in their entireties, U.S. Provisional Patent Application No. 61/782,940, which was filed on Mar. 14, 2013, and U.S. Provisional Patent Application No. 61/869,265, which was filed on Aug. 23, 2013.

TECHNICAL FIELD

In various embodiments, the present invention relates to devices and methods for providing non-invasive therapy to cerebral aneurysms and/or other similar vascular disorders in which an implant (e.g., an embolic micro-coil) is controllably delivered to a lesion and mechanically detached through actuation of a built-in detachment handle/cutting mechanism. In other embodiments, the invention relates to implantable assemblies and, specifically, to a junction connecting a polymeric stretch resistant member to an implantable device (e.g., an embolic micro-coil), as well as to methods of manufacture.

BACKGROUND

A cerebral aneurysm (i.e., an acute subarachnoid hemorrhage) is a cerebrovascular swelling on the wall of an artery that develops because of a congenitally weak cerebral artery or due to arteriosclerosis, a bacterial infection, a head wound, brain syphilis, etc. The cerebral aneurysm may develop suddenly without initial symptoms, and can cause extreme pain. In general, in 15% of cerebral aneurysm cases, the patient dies suddenly upon development of the cerebral aneurysm. In another 15% of cerebral aneurysm cases, the patient dies under medical treatment; and in 30% of cerebral aneurysm cases, the patient survives after treatment but feels an acute aftereffect. As such, a cerebral aneurysm is a very concerning development.

A cerebral aneurysm may be treated through either an invasive therapy or a non-invasive therapy. Of these, the non-invasive therapy typically fills the cerebral aneurysm with a micro-coil. Generally, filling the cerebral aneurysm with the micro-coil causes blood to clot, prevents an additional inflow of blood, and decreases the risk of a ruptured aneurysm (i.e., an embolization). Advantageously, the non-invasive therapy can ease the aftereffects of brain surgery and can shorten hospitalization time.

The system used in the non-invasive therapy typically includes a micro-coil and a delivery pusher for carrying the micro-coil to the patient's cerebral aneurysm. When the micro-coil is properly placed in or near the cerebral aneurysm, an operator (e.g., a physician) separates the micro-coil from the delivery pusher. To initiate detachment of the coil, current micro-coil systems generally require a thermal/power supply (for thermal or electrolytic detachment), or a mechanical detachment handle that is attached to the proximal end of the delivery pusher after the coil is positioned in the aneurysm.

Certain mechanical detachment systems employ the use of a core wire to remove an element that provides an interference fit between a tip of the core wire and some component of the coil. Certain other mechanical detachment systems have used interlocking arms that disengage when advanced beyond the micro-catheter tip, or a ball-screw mechanism that unscrews the coil from a tip of the delivery pusher when the pusher is rotated, or even hydraulic systems that eject the coil from the delivery pusher tip when the inside diameter is pressurized with saline.

Having to attach, however, a mechanical detachment handle (or some other element, such as a power supply box) to the proximal end of the delivery pusher after the coil is positioned in the aneurysm in order to initiate detachment of the coil is problematic. For example, the delivery pusher and thus the coil may inadvertently move while the detachment handle (or other element) is being attached. This may cause the coil to lose its proper placement within or near the cerebral aneurysm. In addition, attaching the detachment handle (or other element) lengthens the operating time. Where a procedure requires many such coils to be delivered, this can add significantly to the overall operating time.

In addition still, currently available implantable devices, such as embolic micro-coils, often employ a polymeric stretch resistant member to maintain the shape of the micro-coil and to prevent it from unfurling during delivery to a patient's body. During manufacture, in order to form a mechanical securement (e.g., a junction) between the stretch resistant member and the micro-coil, the stretch resistant member is generally melted at, and coupled to, one or both end(s) of the micro-coil. The process of melting the polymer can, however, significantly reduce the strength of the stretch resistant member at the junction. As such, when the micro-coil is placed under tension, the melted junction typically, and disadvantageously, fails at a force below the inherent tensile strength of the polymeric stretch resistant member.

Accordingly, needs exist for improved implantable assemblies and for methods of manufacturing and using the same, as well as for improved systems and methods for delivering the implants to a vascular disorder, such as a cerebral aneurysm.

SUMMARY OF THE INVENTION

In various embodiments, the present invention provides a mechanical means of controllably detaching a micro-coil from a delivery pusher. In particular, embodiments of the invention conveniently provide a small, but effective, detachment handle assembly that is fixedly and permanently attached to the proximal end of the delivery device, thereby obviating the procedural step of attaching a handle or other detachment accessory to the delivery pusher in order to initiate the coil's detachment. Such a device is easier to use, does not require any accessories, and simplifies the delivery procedure, particularly for those physicians that do not perform embolization cases as often as others.

In one embodiment, the main junction between the coil and the delivery pusher is created by a polymer suture. As such, the junction is more flexible than the micro-coil junctions of certain prior art devices. The flexible junction improves the ability of the coil to conform within an aneurysmal space, and also improves the safety of the medical procedure by reducing the chance for aneurysm perforation or rupture.

Additionally, embodiments of the present invention provide a mechanical means for "instantaneously" detaching the micro-coil from the delivery pusher. The mechanical means includes a retractable core wire that pulls the detachment suture through a static blade mounted to, or formed within, a tip of the delivery pusher. As further explained below, embodiments of the invention also feature several alternative configurations of attaching the detachment suture to the delivery pusher and for severing the detachment suture from the delivery pusher.

In general, in one aspect, embodiments of the invention feature a device for delivering an implant, such as an embolic coil, to a vascular disorder of a patient, such as a cerebral aneurysm. The device includes a delivery pusher (which has a proximal shaft and a flexible distal shaft) and a stationary blade that is coupled to the flexible distal shaft. The stationary blade includes a sharp and stationary cutting component for cutting through a suture that couples the implant to the delivery pusher and for thereby releasing the implant when placed in proximity to the vascular disorder.

Various embodiments of this aspect of the invention include the following features. The stationary blade may envelope an outer surface of the flexible distal shaft. In addition, a retractable release wire may be positioned within a lumen of the delivery pusher. A coil hook component, which may include a loop of wire, may be coupled to a distal end of the retractable release wire. In one embodiment, the suture extends from the implant, through a portion of the delivery pusher lumen, through the wire loop of the coil hook component, and through a blunt opening in the stationary blade. In such an embodiment, as well as in other embodiments described below, the release wire, when retracted, causes the suture to be retracted towards the blade's sharp and stationary cutting component.

In addition to the blunt opening, the stationary blade may define a channel connecting the blunt opening to the sharp and stationary cutting component. Moreover, the stationary blade may further define a window proximal to the sharp and stationary cutting component. In one particular embodiment, the suture coupling the implant to the delivery pusher (i) is coupled at first and second points to the retractable release wire positioned within the lumen of the delivery pusher, and (ii) extends through the blunt opening and the window defined by the stationary blade. In this embodiment, the device may include a second suture, and the suture coupling the implant to the delivery pusher may be coupled to the implant via that second suture.

A window cutout may also be defined within a wall of the flexible distal shaft, and the blade may be positioned over the window cutout. In addition, a suture locking tube may be coupled to the flexible distal shaft, and a portion of the suture may be locked down between the suture locking tube and the flexible distal shaft. Alternatively, a metal coil may be coupled to the flexible distal shaft, and a portion of the suture may be locked down between the metal coil and the flexible distal shaft.

In another embodiment, a polymer tip is coupled to a distal end of the flexible distal shaft. The stationary blade may be located adjacent the polymer tip. The flexible distal shaft of the embodiments described herein may include a flexible inner shaft, a flexible outer shaft, and an anti-elongation ribbon for preventing unwanted elongation of the flexible distal shaft.

In general, in another aspect, embodiments of the invention feature a device for delivering an implant, such as an embolic coil, to a vascular disorder of a patient, such as a cerebral aneurysm. The device includes a delivery pusher (which has a proximal shaft and a flexible distal shaft) and a detachment handle that includes a user manipulable component for initiating a mechanical release of an implant coupled to the delivery pusher when the implant is placed in proximity to the vascular disorder. The detachment handle may be fixedly and permanently attached to the proximal shaft such that a user of the device need not couple the detachment handle to the delivery pusher.

In various embodiments, a strain relief is coupled to the detachment handle and also envelops a portion of the proximal shaft. In addition, the user manipulable component for initiating the mechanical release of the implant may include a handle slider.

In general, in yet another aspect, embodiments of the invention feature a method for delivering an implant, such as an embolic coil, to a vascular disorder of a patient, such as a cerebral aneurysm. In accordance with the method, the implant (which is coupled via a suture to a delivery pusher) is advanced in proximity to the vascular disorder. The delivery pusher, which may be used in that regard, includes a stationary blade, which itself includes a sharp and stationary cutting component. The suture is then caused to impinge upon the sharp and stationary cutting component, which cuts through the suture. The implant is thereby released in proximity to the vascular disorder.

Again, the stationary blade may envelope an outer surface of the delivery pusher. In addition, the suture may be caused to impinge upon the sharp and stationary cutting component by retracting a release wire coupled to the suture.

In general, in still another aspect, embodiments of the invention feature a method for delivering an implant, such as an embolic coil, to a vascular disorder of a patient, such as a cerebral aneurysm. In accordance with the method, the implant (which is coupled to a delivery pusher) is advanced in proximity to the vascular disorder. The delivery pusher, which may be used in that regard, is fixedly and permanently attached to a detachment handle such that a user need not couple the detachment handle to the delivery pusher. The detachment handle includes a user manipulable component, such as a handle slider, which is actuated to initiate a mechanical release of the implant from the delivery pusher.

In certain other embodiments, the present invention relates to a system that increases the strength of a junction connecting a polymeric stretch resistant member to an implantable device (e.g., an embolic micro-coil) to be equal to or greater than the tensile strength of the stretch resistant member itself, as well as to methods of manufacturing and using the same. In one embodiment, the objective is accomplished without any additional materials or adhesives being employed, thereby simplifying the manufacturing process. The stretch resistant member may, for example, be permanently attached to the micro-coil and be eventually implanted within a patient's body together with the micro-coil. As such, the regulatory acceptance of such an implantable assembly can be simplified.

In one embodiment of the invention, the polymeric stretch resistant member includes two components. One component maximizes the attachment strength to the micro-coil and the other component provides stretch resistance for the micro-coil and attachment to a delivery pusher.

In general, in one aspect, embodiments of the invention feature an implantable assembly. The implantable assembly includes an implantable device and a stretch resistant member. The implantable device (e.g., a coil) includes a proximal end and a distal end and defines a passageway that extends from the proximal end to the distal end, while the stretch resistant member extends along the passageway and is coupled to the distal end at a junction. The stretch resistant member includes first and second components. The second component, which is different from and coupled to the first component, includes multiple strands coupled to the junction and with a coupling strength greater than a tensile strength of the first component.

In various embodiments, the stretch resistant member is coupled to the implantable device at only the distal end. The stretch resistant member may also be coupled to a delivery pusher. The stretch resistant member may include a polymeric material, such as polypropylene. In one embodiment, the first component of the stretch resistant member includes a knot at a distal end thereof. The second component may be knotted around the first component at a point proximal to the knot of the first component.

The multiple strands of the second component (e.g., four strand ends) may extend from the point proximal to the knot of the first component toward the distal end of the implantable device. The multiple strands may also be molded to the distal end to form the junction, which may be an atraumatic tip, such as a ball tip.

In general, in another aspect, embodiments of the invention feature a method of manufacturing an implantable assembly. The method includes the steps of coupling a first component of a stretch resistant member to a second component of the stretch resistant member, and extending the stretch resistant member through a passageway defined by an implantable device, such as a coil. The first and second components may be different from one another, the second component may include multiple strands, and the implantable device may include a proximal end and a distal end. The method further includes the step of coupling the multiple strands of the second component to the distal end of the implantable device at a junction and with a coupling strength greater than a tensile strength of the first component.

In various embodiments of this aspect of the invention, the stretch resistant member includes a polymeric material, such as polypropylene. Coupling the first component to the second component may be accomplished by forming a knot at a distal end of the first component, and then knotting the second component around the first component at a point proximal to the knot of the first component. The multiple strands of the second component (e.g., four strand ends) may be extended from the point proximal to the knot of the first component toward the distal end of the implantable device.

Coupling the multiple strands of the second component to the distal end of the implantable device may be accomplished by melting distal ends of the multiple strands and molding the melted distal ends to the distal end of the implantable device to form the junction. The junction may include an atraumatic tip, such as a tip ball.

The above-described method may also include the step of coupling the stretch resistant member to a delivery pusher.

These and other objects, along with advantages and features of the embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

In the following description, various embodiments of the present invention are described with reference to the following drawings, in which:

FIG. 2 schematically illustrates a portion of the delivery device's delivery pusher in accordance with one embodiment of the invention;

FIG. 8A schematically illustrates a side view of the single suture configuration of the embolic coil, heat set into a secondary coil shape, in accordance with one embodiment of the invention;

FIG. 8B schematically illustrates a front view of the single suture configuration of the embolic coil, heat set into the secondary coil shape, in accordance with one embodiment of the invention;

FIG. 9A schematically illustrates a side view of a double suture configuration of an embolic coil in accordance with one embodiment of the invention;

FIG. 9B schematically illustrates a cross-sectional view of the double suture configuration of the embolic coil in accordance with one embodiment of the invention;

FIGS. 18-28 schematically illustrate various embodiments of blades for severing a suture in accordance with the invention;

DESCRIPTION

In broad overview, embodiments of the present invention feature a device for delivering an implant (e.g., an embolic coil) to a vascular disorder of a patient, such as a cerebral aneurysm. The overall delivery device 100 is shown at the bottom of each of FIGS. 1-6. In addition, in each of FIGS. 1-6, a portion of the overall delivery device 100 is delineated in phantom, and that delineated portion is depicted in greater detail above the depiction of the overall delivery device 100.

Figure 1:
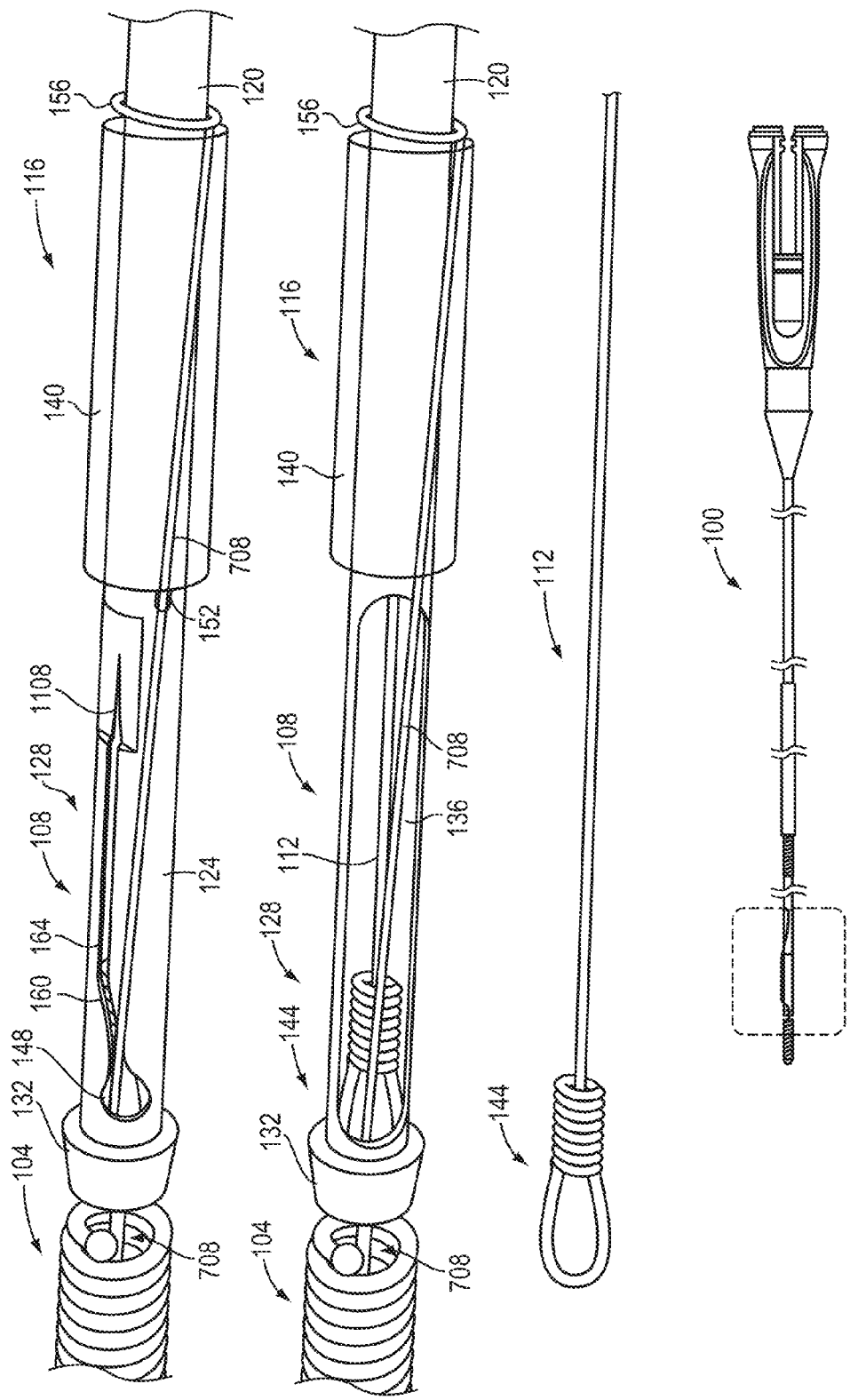
FIG. 1 schematically illustrates various components at a distal portion of a delivery device in accordance with one embodiment of the invention.

As shown in FIG. 1, an embolic coil 104 is attached to a delivery pusher 108 of the delivery device 100. The delivery pusher 108 contains, within a lumen thereof, a retractable release wire 112. As shown in FIGS. 7A-10B, in one embodiment the embolic coil 104 includes a primary coil (see FIGS. 7A-7B and 9A-9B) wound from metallic wire (preferably Platinum 8% Tungsten) that is heat set into a secondary coil shape (see FIGS. 8A-8B and 10A-10B). The embolic coil 104 is made stretch resistant by melting a ball 704 of polymer (preferably monofilament polypropylene) suture 708 at a distal end 712 of the coil 104 and threading the suture 708 through a proximal end 716 of the primary coil 104. The suture 708 is preferably sized so as to have a United States Pharmacopeia ("USP") 9-0 suture designation, which means that the suture 708 typically has a diameter between 0.0012" and 0.0017". In other configurations, however, the suture 708 may be smaller or larger and/or be made of other polymers. As shown in FIGS. 9A-9B and 10A-10B, the suture 708 may be doubled through the inside diameter of the primary coil or, as shown in FIGS. 7A-7B and 8A-8B, only a single strand of the suture 708 may extend through the primary coil. The termination of the double suture configuration can be a knot 904 created between the two strands within the inside diameter of the primary coil. In either the single or double suture configuration, the preferred design is to have only a single strand exiting the primary coil inside diameter into the delivery pusher 108 as it is desirable to only sever a single strand during detachment actuation. Alternate designs for connecting the coil to the delivery pusher are discussed further below.

Figure 3:
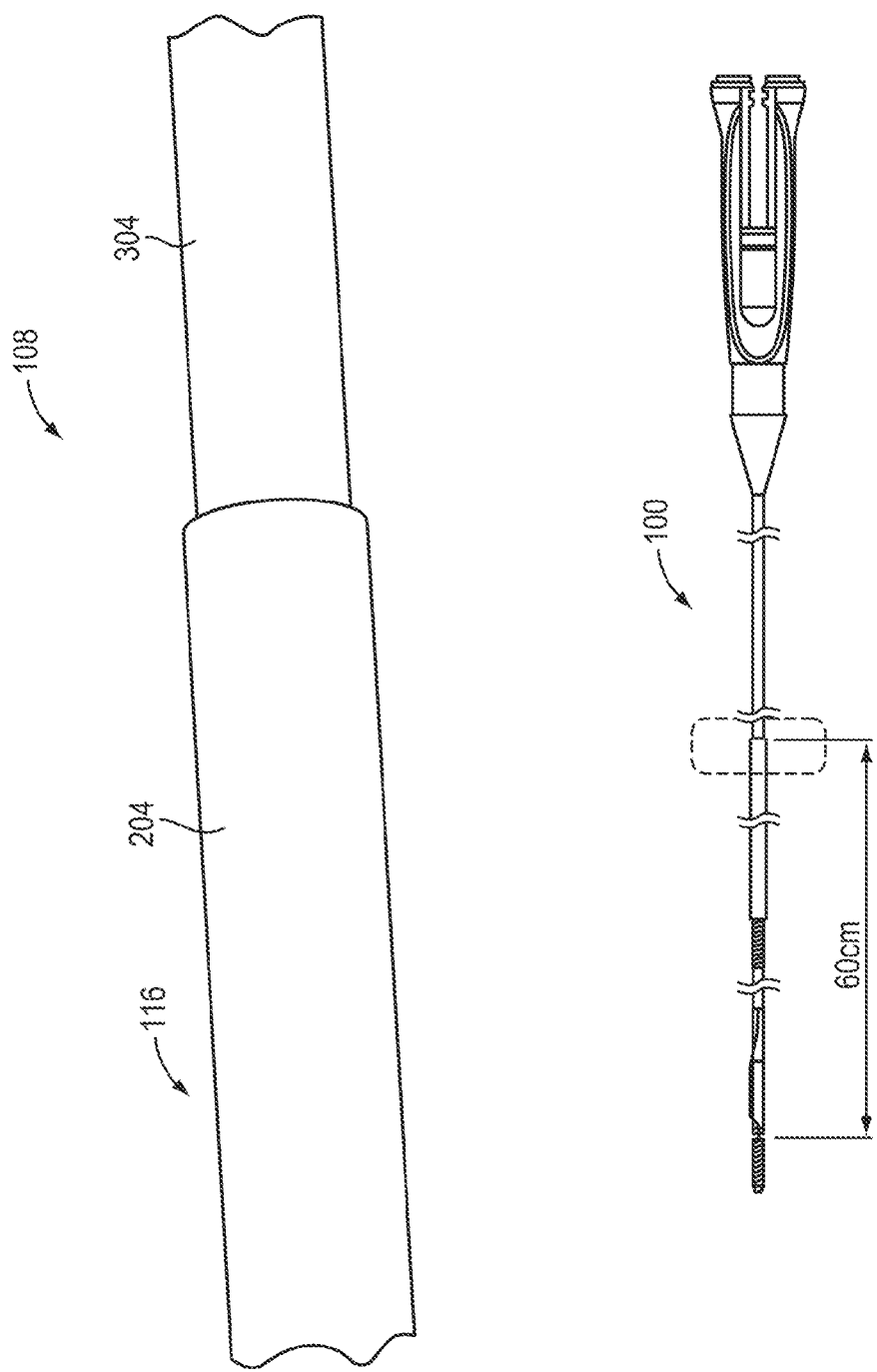
FIG. 3 schematically illustrates another portion of the delivery device's delivery pusher in accordance with one embodiment of the invention.

The delivery pusher 108 includes a proximal shaft 304 (see FIGS. 3-6) and a flexible distal shaft 116 (see FIGS. 1-3). The proximal shaft 304 may be made from rigid, metal hypotube, preferably 300 series stainless steel with a wall thickness of about 0.002" to provide good pushability during coil 104 delivery and stability during detachment actuation. The flexible distal shaft 116 includes a flexible inner shaft 120 made from a rigid thin-walled polymer (preferably PEEK with a wall thickness of about 0.001"), a flexible outer shaft 204 made from a rigid thin-walled polymer (preferably PEEK with a wall thickness of about 0.001"), and an anti-elongation component 208 (made preferably from 300 series stainless steel ribbon).

As shown in FIG. 1, a stationary blade 124 (preferably 300 series stainless steel) may be attached to a distal end 128 of the flexible inner shaft 120 with an adhesive. The blade 124 may be located behind a polymer delivery pusher tip 132 (preferably pebax-polyether block amide), which is intended to provide an atraumatic interface and help secure the blade 124 to the flexible inner shaft 120. The flexible inner shaft 120 has a window cutout 136 at the distal end 128 thereof that allows the suture 708 to move within the laser-cut geometry of the blade during detachment. This window 136 may be hand cut, machine cut, ground, or laser cut. Located proximal to the blade 124 is a suture locking tube 140, which is a short length of polymer (preferably heat-shrink polyethylene terephthalate (PET)) that helps lock down the detachment suture 708 to the flexible inner shaft 120.

With reference still to FIG. 1, located inside the delivery pusher 108 is the retractable release wire 112. The retractable release wire 112 includes a core wire (preferably 300 series stainless steel), which is ground on the distal end, is between 35 cm to 75 cm (preferably about 60 cm) in length, and is coated on the unground section with, for example, polytetrafluoroethylene (PTFE) to reduce friction. Preferably, the core wire is about 0.006" in diameter, and ground to about 0.002" at the tip. A coil hook component 144, preferably made from 300 series stainless steel with about 0.001" diameter wire, may be created by winding a segment of wire into a short coil of about 1 mm and a short "hook" and soldering these components in the shape shown in FIG. 1 to the tip of the retractable release wire 112.

As also shown in FIG. 1, the detachment suture 708 extends from the primary coil 104, is threaded through an inside diameter of the delivery pusher 108 tip 132, through the loop of the coil hook 144, and through a front opening 148 of the attached blade 124, is aligned with a notch 152 (see also FIG. 18) in the proximal end of the blade 124, and is attached to the flexible inner shaft 120 by the suture locking tube 140. Additionally, the proximal end of the suture 708 may be tied into a knot 156 around the flexible inner shaft 120 and adhesive may be applied to the knot 156, or the knot 156 may be slightly melted to further secure the suture 708 in position.

Figure 6:
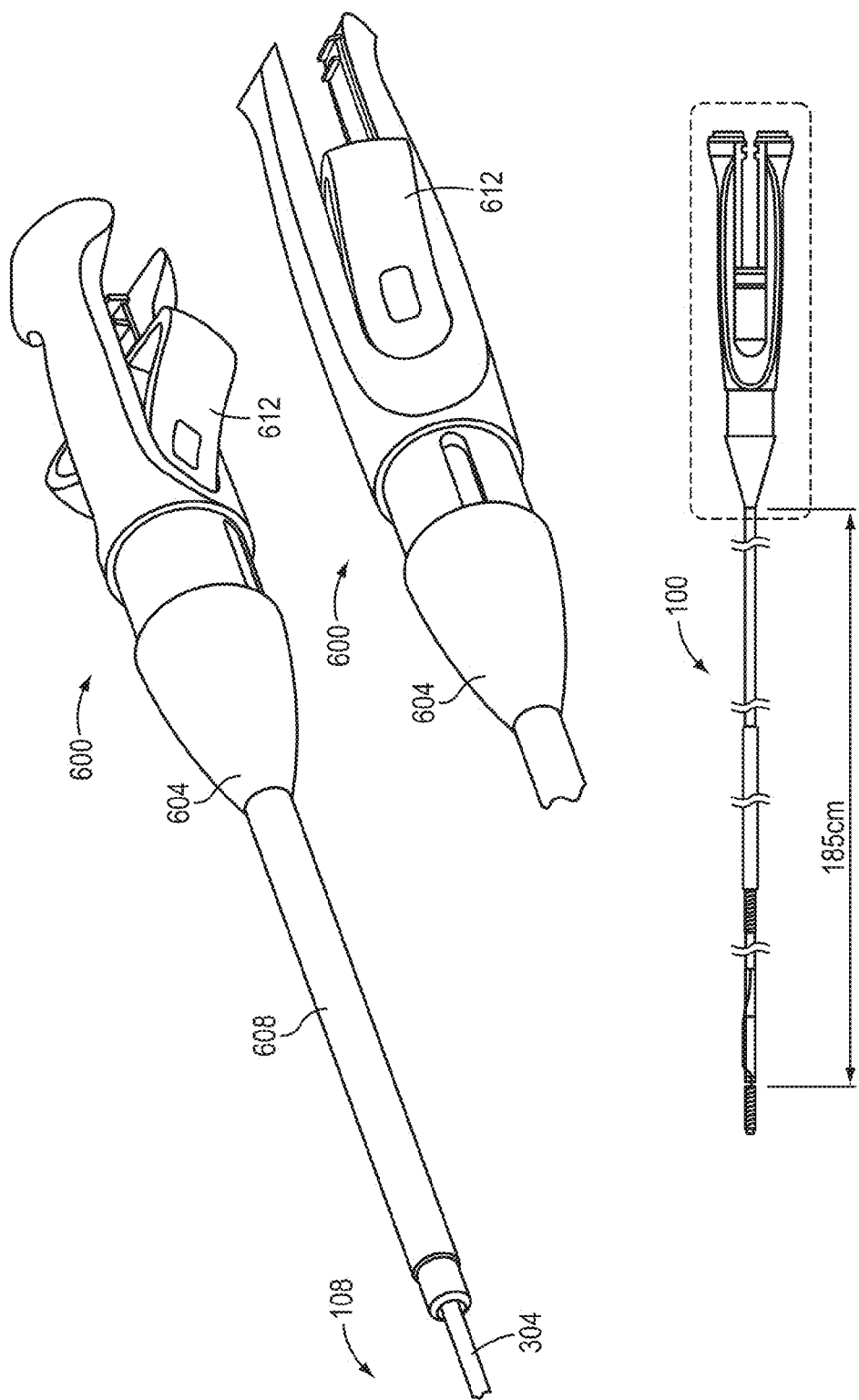
FIG. 6 schematically illustrates various components at a proximal portion of the delivery device, including a detachment handle, in accordance with one embodiment of the invention.
Figure 7A:
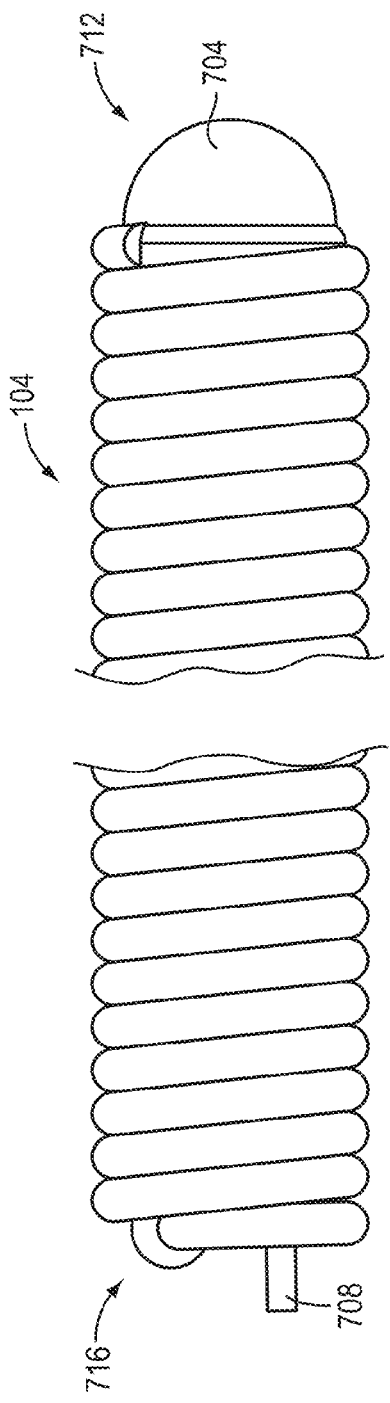
FIG. 7A schematically illustrates a side view of a single suture configuration of an embolic coil in accordance with one embodiment of the invention.
Figure 7B:
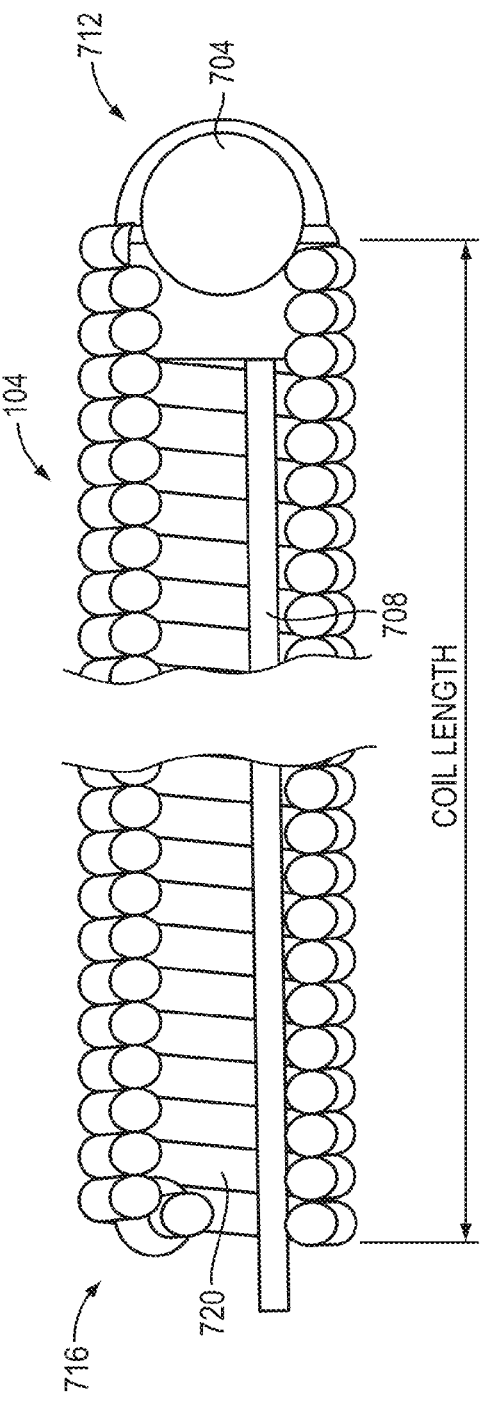
FIG. 7B schematically illustrates a cross-sectional view of the single suture configuration of the embolic coil in accordance with one embodiment of the invention.
Figure 10B:
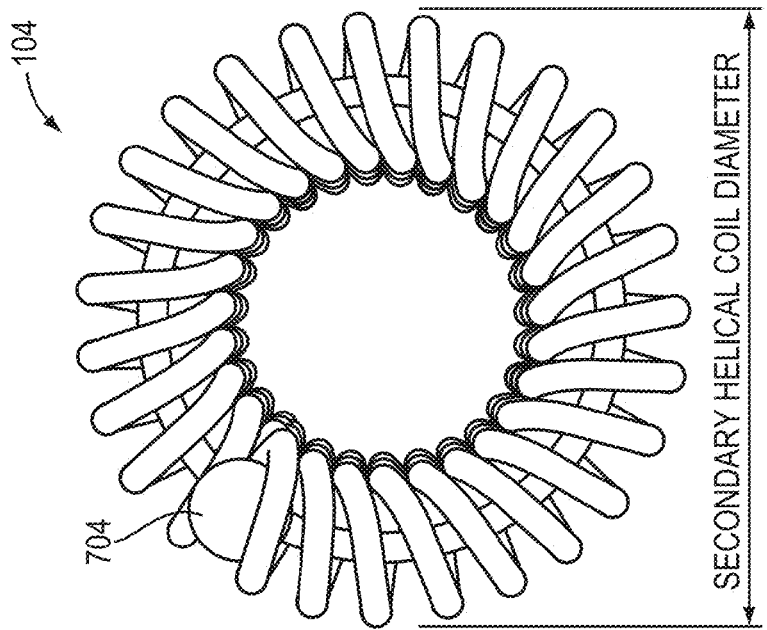
FIG. 10B schematically illustrates a front view of the double suture configuration of the embolic coil, heat set into the secondary coil shape, in accordance with one embodiment of the invention.
Figure 10A:
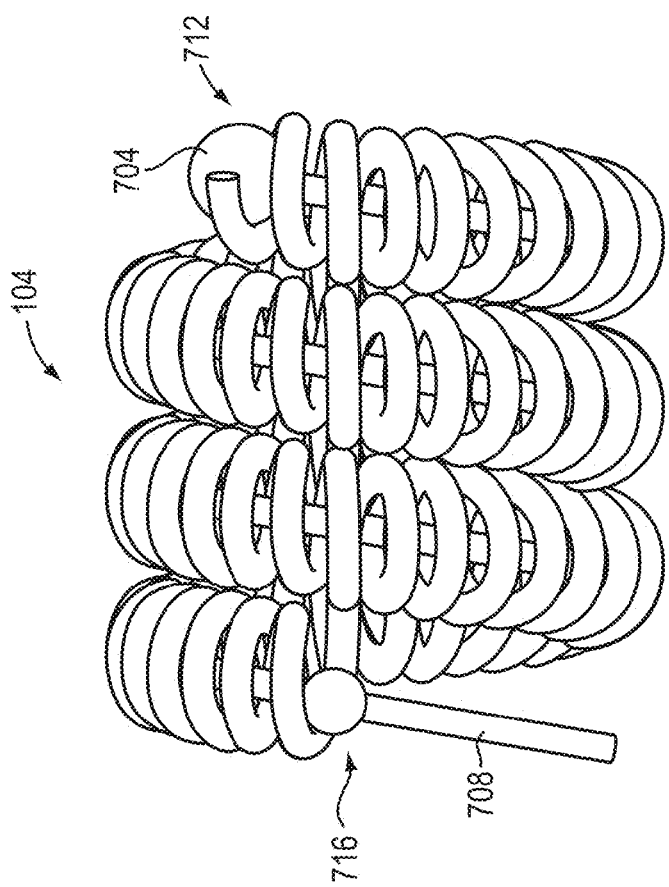
FIG. 10A schematically illustrates a side view of the double suture configuration of the embolic coil, heat set into a secondary coil shape, in accordance with one embodiment of the invention.

With reference now to FIG. 6, the proximal shaft 304 is connected to a handle body 604 of a detachment handle 600 by inserting the proximal shaft 304 into a cavity in the injection molded handle body 604 and by applying adhesive or press fitting the connection. As such, following manufacture, the detachment handle 600 is fixedly and permanently attached to the proximal shaft 304 such that a user of the device (e.g., a physician) need not himself or herself couple the detachment handle 600 to the delivery pusher 108 for any reason, including to initiate detachment of the micro-coil 104 from the delivery pusher 108. As also shown in FIG. 6, a strain relief 608 (preferably made from pebax) may be employed to help prevent kinking at the junction of the proximal shaft 304 and handle body 604.

The handle body 604 may include one or more injection molded parts, preferably made from acrylonitrile butadiene styrene (ABS). A proximal end of the retractable release wire 112 may be secured to a handle slider 612 of the detachment handle 600, for example by threading the wire 112 through a channel in the handle slider 612 and bending the wire 112 to form a mechanical hook bond within the handle slider 612. Adhesive may also be applied to secure these two components together. Upon manufacturing the delivery device 100, the handle body 604 and handle slider 612 may be assembled in a "locked" position, in which the retractable release wire 112 and coil hook 144 are locked in position relative to the blade 124. These parts may be held in place by detent features molded into the handle body 604 and handle slider 612 mating surfaces.

In other embodiments, rather than featuring the handle slider 612, the detachment handle 600 may instead feature another user manipulable component for initiating the mechanical release, as described herein, of the embolic coil 104. For example, the detachment handle 600 may feature a mechanical trigger, a mechanical push-button, or other mechanical component that requires mechanical input from a user of the device (e.g., a physician) in order to initiate the mechanical detachment of the embolic coil 104.

Figure 4:
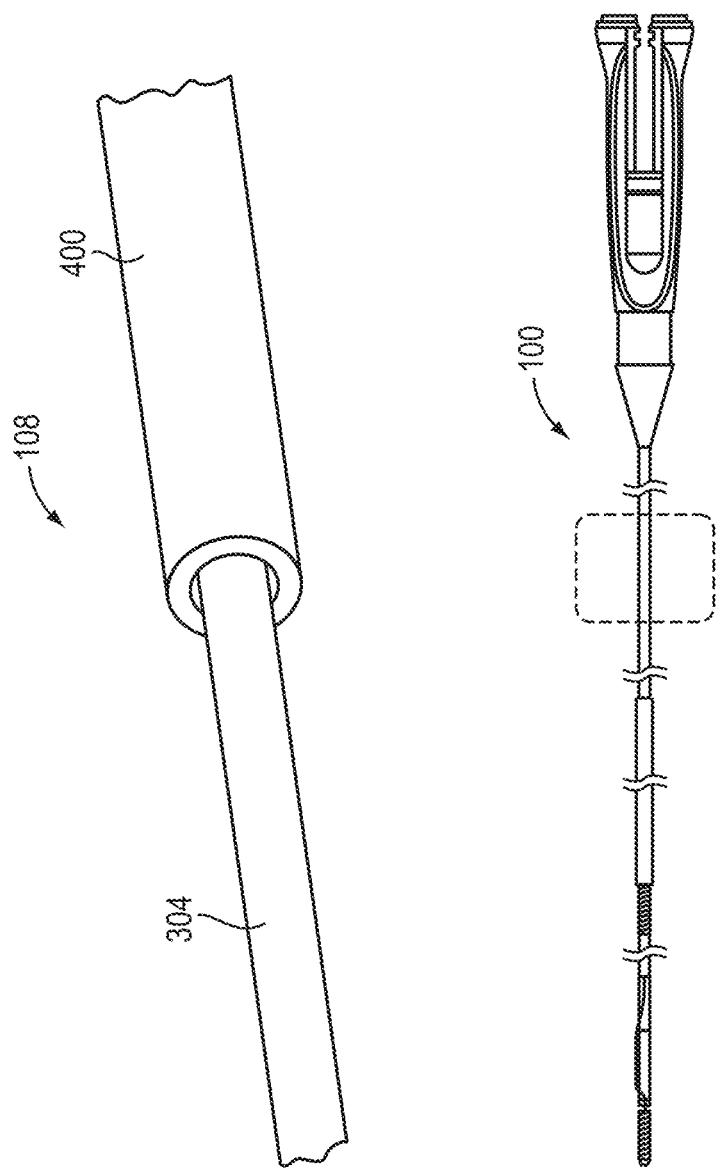
FIG. 4 schematically illustrates yet another portion of the delivery device's delivery pusher in accordance with one embodiment of the invention.
Figure 5:
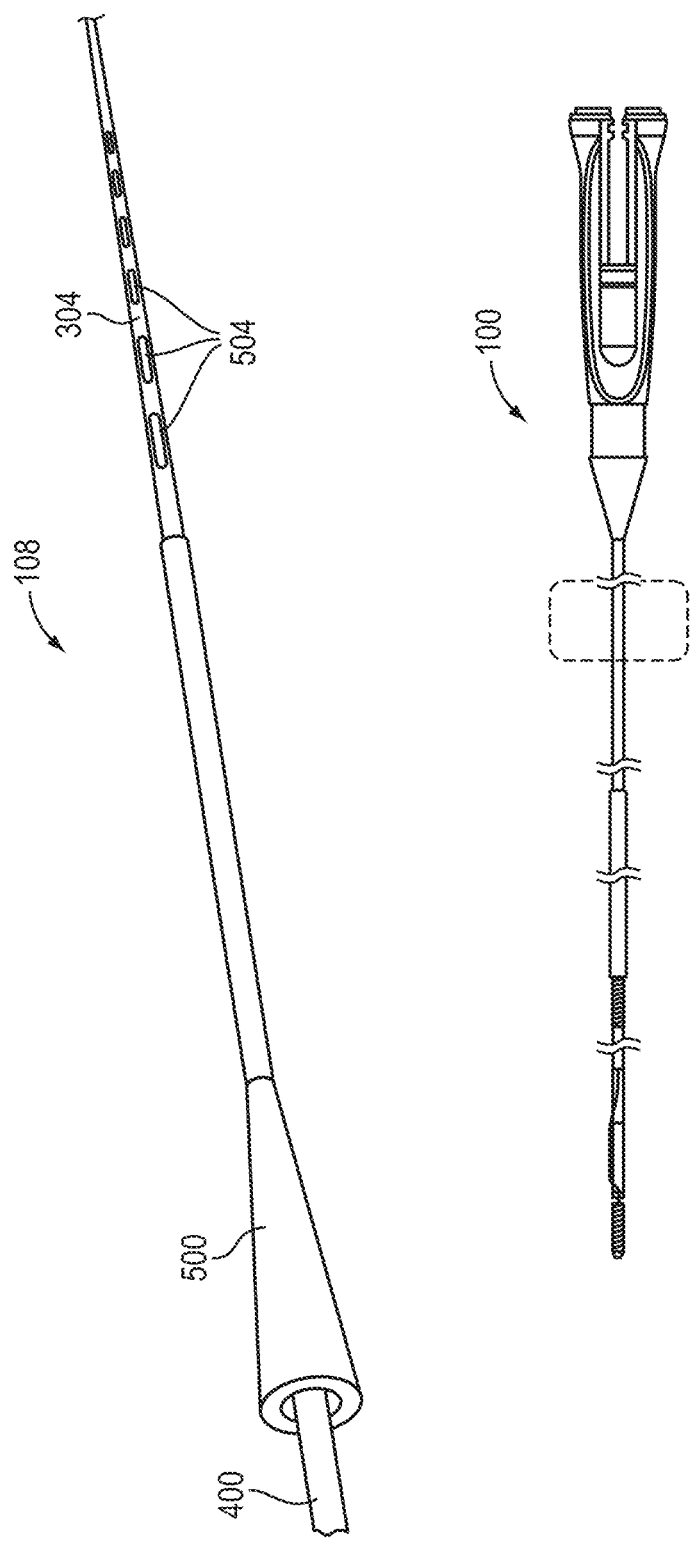
FIG. 5 schematically illustrates still another portion of the delivery device's delivery pusher in accordance with one embodiment of the invention.

FIGS. 4 and 5 show an introducer sheath 400, which protects the micro-coil 104 during sterilization and shipment, and a proximal locking tube 500, which locks the introducer sheath 400 in place on the proximal shaft 304. FIG. 5 also shows proximal shaft markings 504, which preferably are laser-etched into the proximal shaft 304 hypotube. The function of these markings 504 is to designate to the user, during introduction of the micro-coil 104 into a micro-catheter, the position of the micro-coil 104 relative to the micro-catheter tip to save fluoroscopy time and to reduce unnecessary x-ray radiation to the patient.

Figure 11:
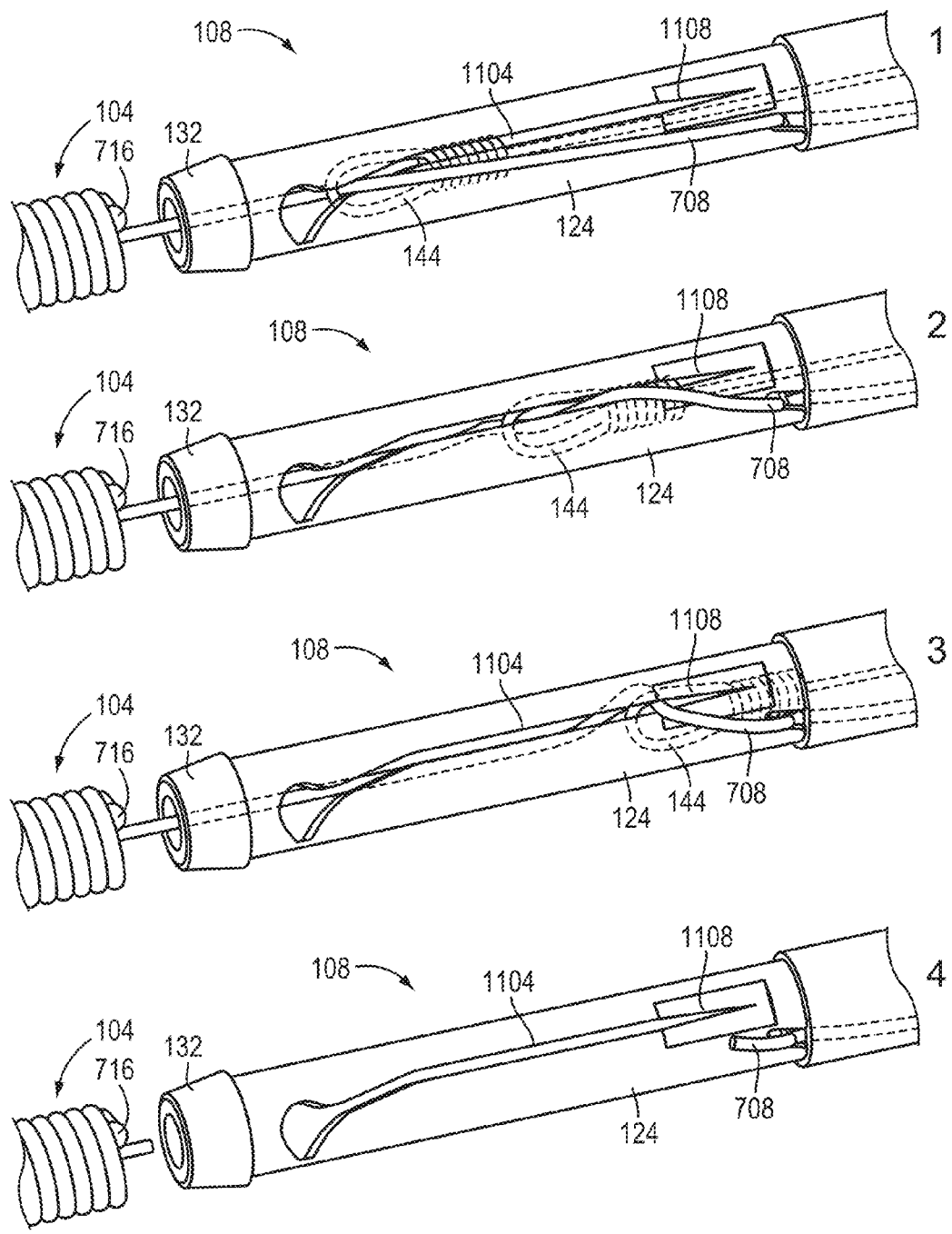
FIG. 11 schematically illustrates a series of steps for releasing an embolic coil from a delivery device in accordance with one embodiment of the invention.

FIG. 11 depicts the manner by which the suture 708 may be severed so as to release the micro-coil 104 from the delivery pusher 108. The detachment handle 600 is intended to be held by the user like a syringe, with thumb placed on a proximal end of the handle 600 and index and middle fingers straddling the handle body 604 with the index and middle fingertips placed on either side of the handle slider 612. Since the suture strand 708 extending from the embolic micro-coil 104 is threaded through the coil hook 144, which is attached to the retractable release wire 112, when the release wire 112 is retracted (by retraction of the handle slider 612), the coil hook 144 pulls the suture 708 through an open channel 1104 of the blade 124 and into a sharp section 1108 of the blade 124 (i.e., a sharp and stationary cutting component 1108), thereby severing the suture 708 and releasing the coil 104 from the delivery pusher 108 tip 132. In this preferred configuration, there is a slight gap between the proximal end 716 of the micro-coil 104 and the delivery pusher 108 tip 132. During detachment, the micro-coil 104 tends to move backward slightly, but the diameter of the proximal end 716 of the micro-coil 104 is nearly identical to the diameter of the deliver pusher 108 tip 132. This configuration allows the proximal end 716 of the micro-coil 104 to contact the surface of the delivery pusher 108 tip 132, but prevents the micro-coil 104 from entering the inside diameter of the delivery pusher 108 tip 132. After the suture 708 is severed, the slight compressive force that exists between the proximal end 716 of the micro-coil 104 and the delivery pusher 108 tip 132 tends to nudge the micro-coil 104 away from the delivery pusher 108 tip 132.

As shown in FIG. 2, an anti-elongation ribbon 208 is employed to prevent the coil 104 from prematurely (and thus undesirably) detaching from the delivery pusher 108 prior to detachment actuation. In particular, although the flexible distal shaft 116 utilizes rigid polymer members (for stability during mechanical detachment), it also needs to provide enough flexibility and low-friction to access the neurovasculature through a micro-catheter. As such, the flexible distal shaft 116 is more susceptible to elongation than the metal proximal shaft 304 or the retractable release wire 112. Since the flexible distal shaft 116/proximal shaft 304 assembly and the retractable release wire 112 are connected at the proximal end of the delivery pusher 108, within the proximal detachment handle 600, if the delivery device 100 encounters friction during delivery the proximal shaft 304 and retractable release wire 112 will likely retract at the same rate, but the flexible distal shaft 116 will elongate at a greater rate. If the flexible distal shaft 116 elongates at a greater rate than the retractable release wire 112 and proximal shaft 304, in effect the coil hook 144 will pull the detachment suture 708 into the blade 124, severing the suture 708 and prematurely detaching the coil 104 from the delivery pusher 108. To prevent this from happening, the anti-elongation ribbon 208 is attached between (and to both of) the flexible distal shaft 116 and a radiopaque marker 212, which is itself attached to the outside of the flexible distal shaft 116, by use of an adhesive or solder or both. The anti-elongation ribbon 208 prevents unwanted elongation of the flexible distal shaft 116 during retraction of the delivery pusher 108 inside the micro-catheter.

Several laser-cut blade 124 iterations have been developed for various performance advantages. In the preferred design illustrated in FIGS. 1 and 18, the large round opening 148 in the distal part of the blade 124 allows for easy insertion of the suture 708 from the end hole of the delivery pusher 108 during manufacturing. The width of the laser-cut, angled "neck" or channel 160 of the blade 124 is slightly smaller than the suture 708 thickness to help prevent the suture 708 from inadvertently sliding backward into the straight portion 164 of the laser-cut channel. The angle of the neck 160 is also intended to help prevent inadvertent suture 708 movement into the straight channel 164 during normal use of the micro-coil 104/delivery pusher 108 system. The straight portion 164 of the laser-cut channel is preferably equal to or slightly wider than the suture 708 diameter to allow quick, unrestricted movement of the suture 708 through the channel 164 into the sharp portion 1108 of the blade during detachment actuation. The length of the straight portion 164 of the laser-cut channel also allows the retractable release wire 112 to move backward slightly, relative to the flexible distal shaft 116 during normal advancement and retraction of the delivery pusher 108, subject to frictional forces between the delivery pusher 108 and the micro-catheter. A minimum length in this straight portion 164 of the channel, therefore, provides additional safety and prevention against inadvertent suture 708 movement and premature detachment.

As explained below, the portion 1108 of the blade 124 that is intended to sever and cut the suture 708 has several features that optimize cutting. Optimization of cutting is generally employed herein to mean minimizing the force required to cut the suture 708 in the blade 124. The advantages of minimizing the cut force include reducing movement of the delivery pusher 108 tip 132 and coil 104 during detachment, and creating a gentler separation of the micro-coil 104 from the delivery pusher 108.

Cut force minimization has been achieved by creating a blade geometry that increases the slice-push ratio. Slicing requires that the blade be displaced with some velocity parallel to the cutting edge, while pushing (or chopping) requires that the blade be displaced with some velocity perpendicular to the cutting edge. It is well known in the science/engineering of cutting materials that slicing, or cutting in more of a sideways motion, is easier (and requires less force) than does chopping at a right angle to the material. In other words, slicing requires less energy to cut through a given cross section of material than does chopping, which has the maximum normal force of the blade edge to the cross section to be cut.

Figure 18:
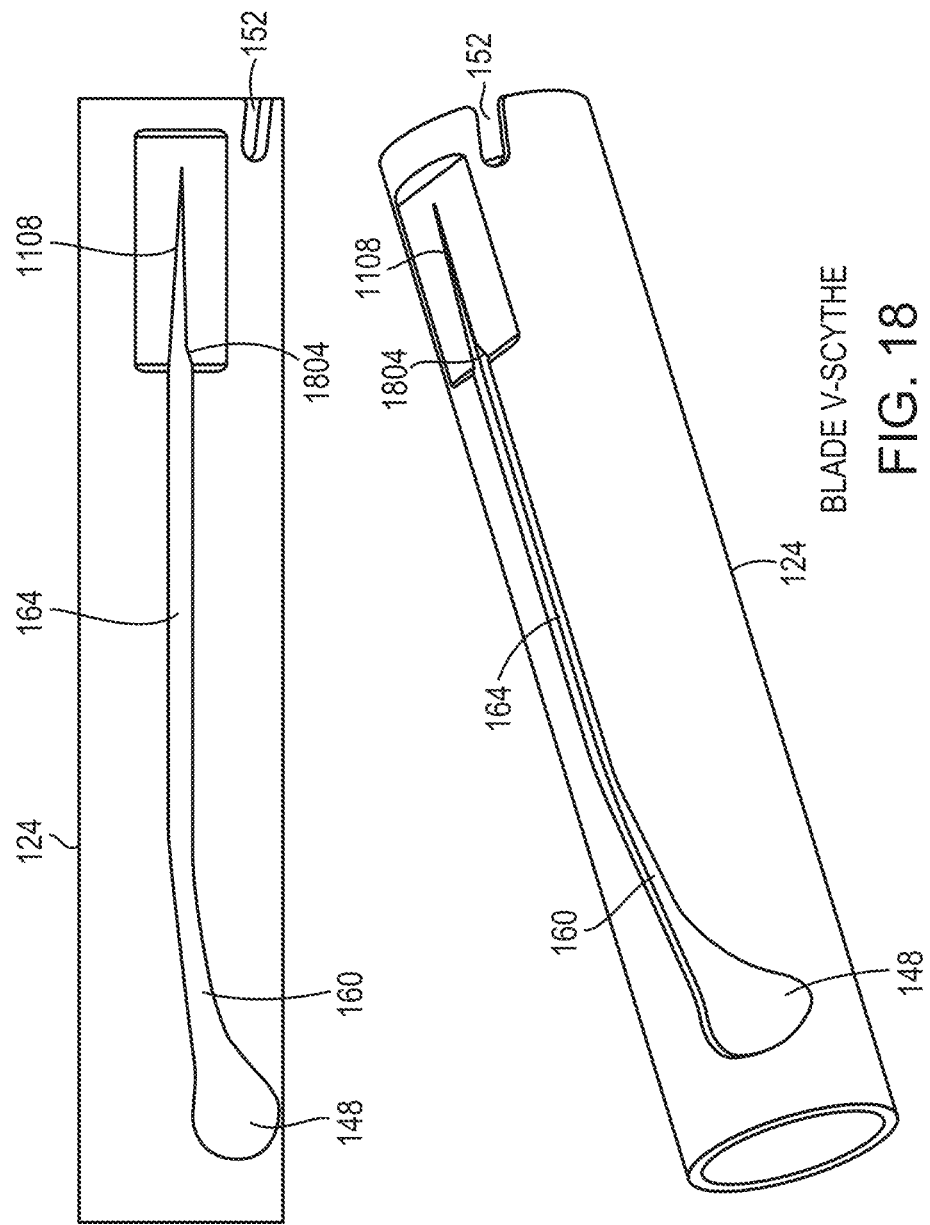

In one embodiment, as illustrated in FIG. 18, the blade 124 geometry for cutting the suture 708 has the following features in the sharp section 1108 of the blade 124:

1) a converging V-shape, which has at least one sharp edge, and converges the suture 708 to progressively become smaller in cross section as it is pulled backward through the V-shape;
2) a tooth or edge 1804 on the sharp side or both sides of the V-shape, near the entrance of the V-shape, to initiate a cut or cuts in the side of the suture 708;
3) a length of the V-shape that is long enough to slice through the suture 708 cross section (if the V-shape is too short or shallow, then this essentially chops the suture 708, which increases the cut force); and
4) a thinning out of the wall of the blade 124 in the sharp section 1108, again to reduce the force required to force the suture 708 through the V-shape (less surface area of the blade 124 dragging on the suture 708 will equate to less force).

Various other blade 124 geometries that have some of the elements described above in order to cut the suture 708 with low force have also been prototyped. These are shown in FIGS. 19-28. Blade 124 designs C (FIG. 19), V (FIG. 20), and CV (FIG. 21) have sharp edges of various geometries, but generally are shorter than desirable. If the edge is made thin enough (and sharp enough) it can still cut efficiently. Blade 124 design CV Extended (FIG. 22) features a longer straight channel that allows increased velocity in pulling the suture 708 backward. The Peanut (FIG. 23) and V-Returns (FIG. 24) blade 124 designs have longer straight channels for increased velocity and also converging edges to cut more efficiently. The Snake (FIG. 25) blade 124 design forces the suture 708 to be pulled through twisting edges, making cuts on either side of the suture 708, but may increase the normal forces depending on the angle of the snake pattern. Also, the Peanut (FIG. 23), V-Returns (FIG. 24), and Snake (FIG. 25) blades 124 have a bottom half of a distal end of the blade 124 removed, which is an alternative approach that may be used to make the delivery pusher 108 tip 132 softer (through the absence of this material).

FIG. 26 shows a Seahorse design for the blade 124, which has elements of the preferred design (i.e., the V-scythe design depicted in FIG. 18) and also a proximal window 2604 to allow for the coil suture 1404/detach suture 1408 configuration shown in FIG. 14 and discussed below. The Band design for the blade 124 depicted in FIG. 27 essentially features only the sharp section 1108 of the blade 124, which is the portion that actually cuts the suture 708, thereby allowing the entire blade 124 length to be shortened. Using this design typically requires that the flexible inner shaft 120 have the features in the omitted portion of the blade 124 (e.g., the large round opening 148 to thread the suture 708 through, the angled neck 160, and the straight channel 164). However, this alternative can make the delivery pusher 108 tip 132 softer and more flexible. The Scythe design of the blade 124 depicted in FIG. 20 has almost all the same elements as the V-scythe design depicted in FIG. 18, but the sharp portion 1108 terminates into a round edge 2804, which is intended to provide a final cut to whatever small cross section of suture 708 may remain after being pulled through the skinny sharp channel 2808 of the sharp portion 1108.

Figure 12:
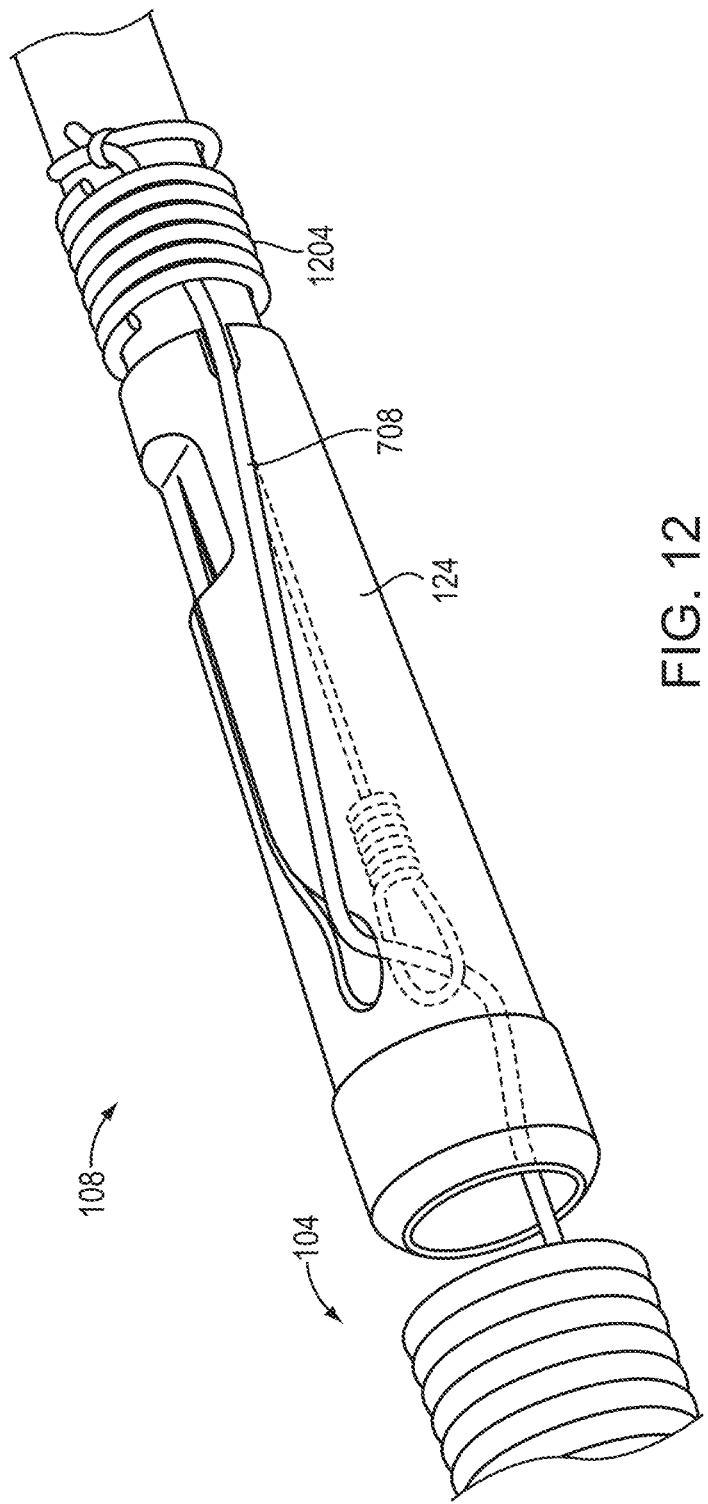
FIGS. 12-14 schematically illustrate various alternative embodiments for attaching a micro-coil to a delivery pusher in accordance with the invention.
Figure 13:
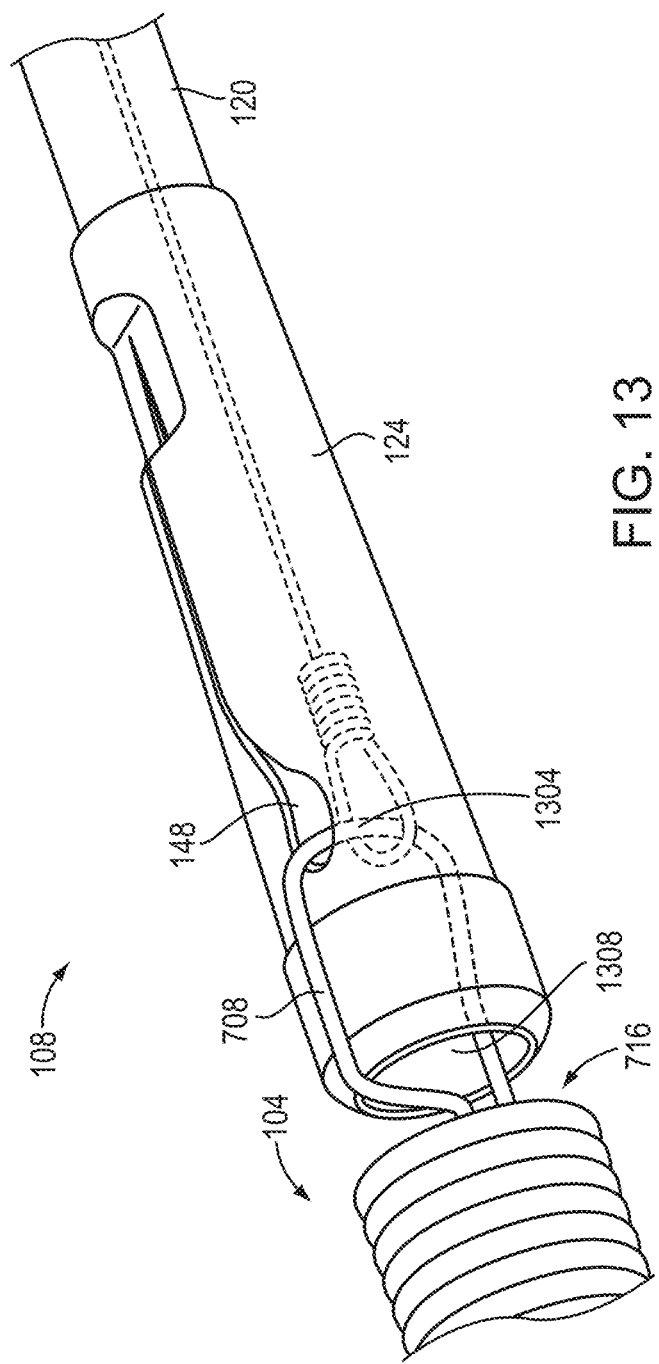
Figure 14:
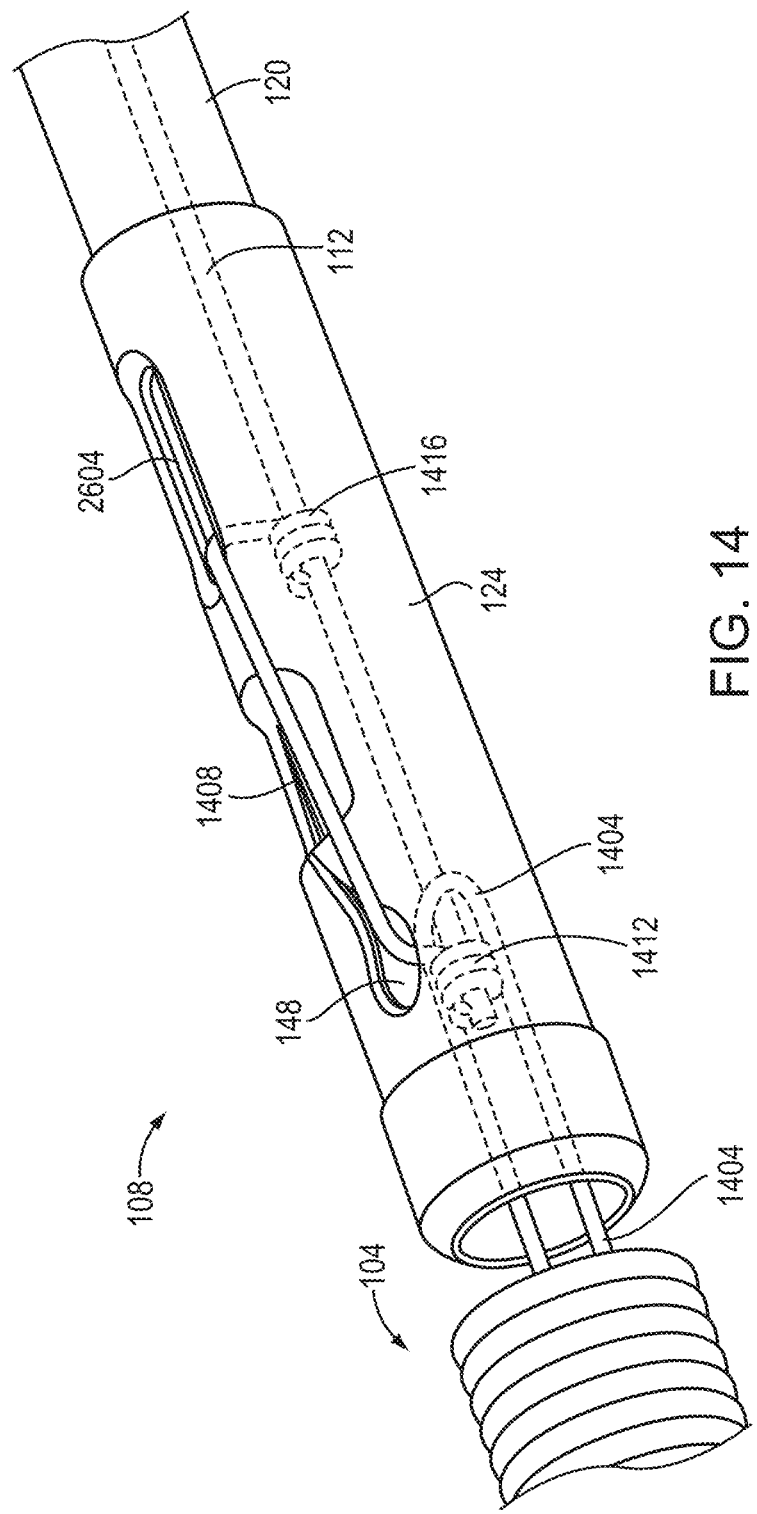

Various other designs for attaching the micro-coil 104 to the delivery pusher 108 are depicted in FIGS. 12-14. In particular, FIG. 12 shows an alternate way of attaching the detachment suture 708 to the delivery pusher 108 by threading the suture 708 underneath a metal coil 1204 (preferably 300 series stainless steel) that is proximal to the blade 124, instead of using the heat-shrink tubing 140. Adhesive may be applied to the metal coil 1204 and suture 708 to secure both components together.

FIG. 13 shows an alternative way for connecting the micro-coil 104 to the delivery pusher 108 by threading a double suture 708 configuration within the inside diameter of the primary (e.g., platinum) coil 104 and creating a suture loop 1304 that protrudes from the proximal end 716 of the primary coil 104. In this embodiment, the manufacturing procedure is modified to loop the suture 708 through the inside of the end hole 1308 of the delivery pusher 108, through the opening in the flexible inner shaft 120, through the front opening 148 of the blade 124, and then back through the inside diameter of the primary coil 104. One advantage of this design is that it obviates the need to attach the suture 708 to the delivery pusher 108, thereby simplifying this portion of the manufacturing process.

FIG. 14 shows yet another micro-coil 104 attachment configuration that uses a double-suture on the inside diameter of the micro-coil ("coil suture 1404") and a separate suture ("detach suture 1408"). The detach suture 1408 may be made of the same material as the coil suture 1404 or of other polymer material suitable for cutting. In this configuration, the retractable release wire 112 has two "stopper" coils 1412, 1416 attached to the tip of the core wire, by solder or adhesive, with a small space between them. These coils 1412, 1416 may be made of a metal such as 300 series stainless steel or platinum alloy. The detach suture 1408 is first connected to the retractable release wire 112 behind the front stopper coil 1412, for example by tying a knot and applying adhesive or melting it slightly. The detach suture 1408 is then looped through the coil suture loop 1404 and pushed through the top front opening 148 of the blade 124 and then through the proximal window 2604 of the blade 124. This end of the detach suture 1408 is then connected to the retractable release wire 112 behind the proximal stopper coil 1416, for example by using a method similar to the first detach suture 1408 connection. The purpose of the proximal window 2604 is to allow an assembler to attach the detach suture 1408 behind the proximal stopper coil 1416. Instead of having the proximal window 2604 in the blade 124 (which increases the total blade 124 length), the window 2604 may alternatively be placed in the flexible inner shaft 120, behind the blade 124.

Figure 15:
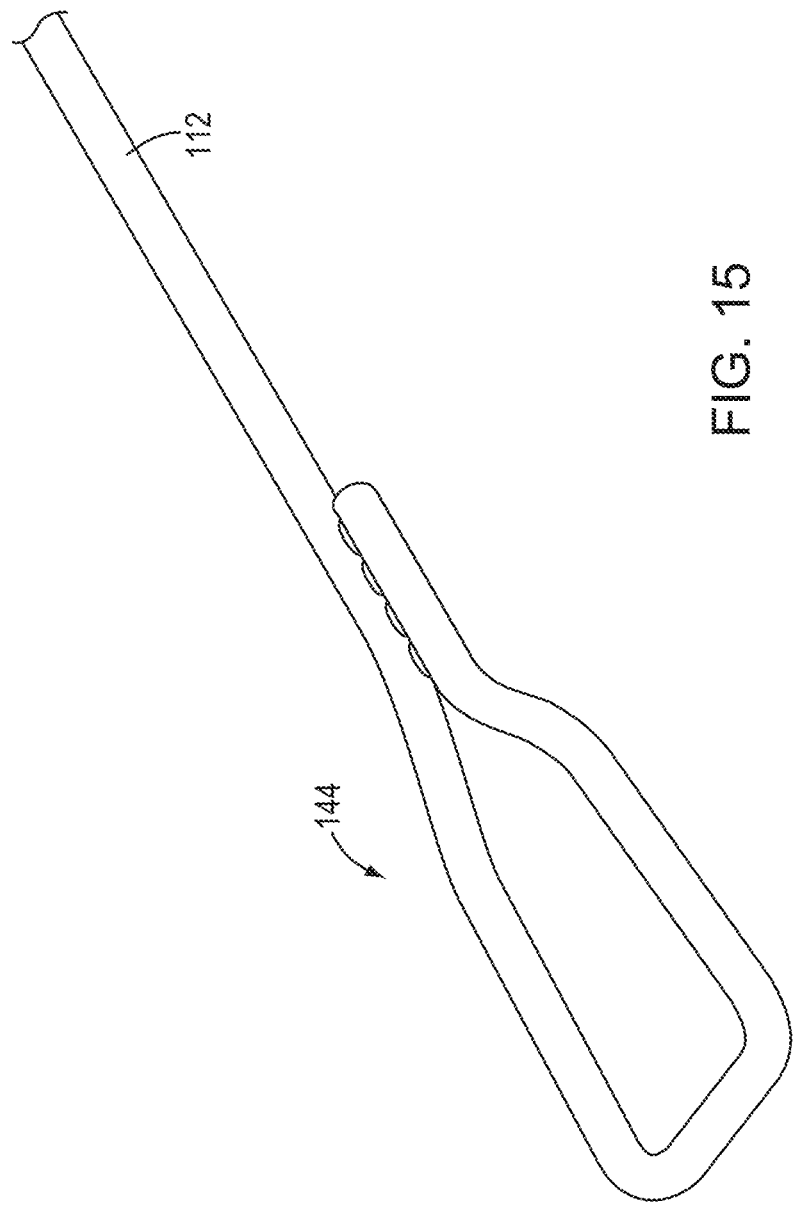
FIGS. 15-17 schematically illustrate various embodiments of a coil hook in accordance with the invention.
Figure 16:
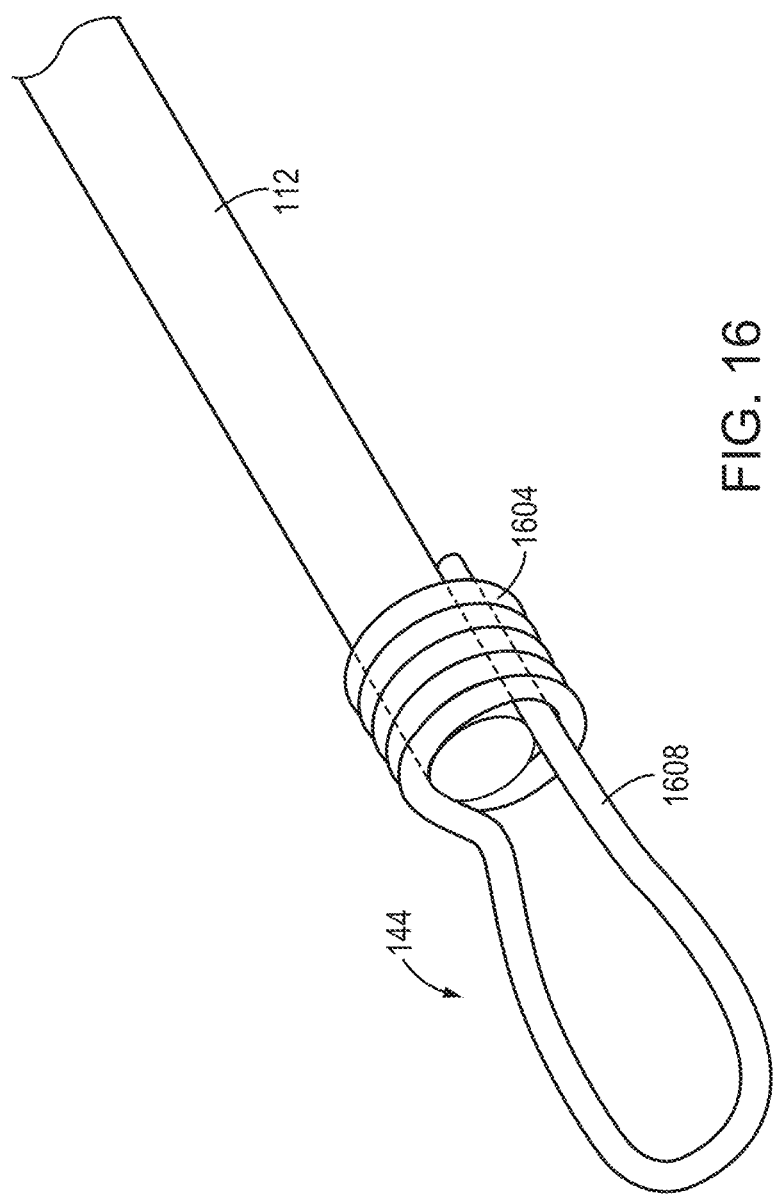
Figure 17:
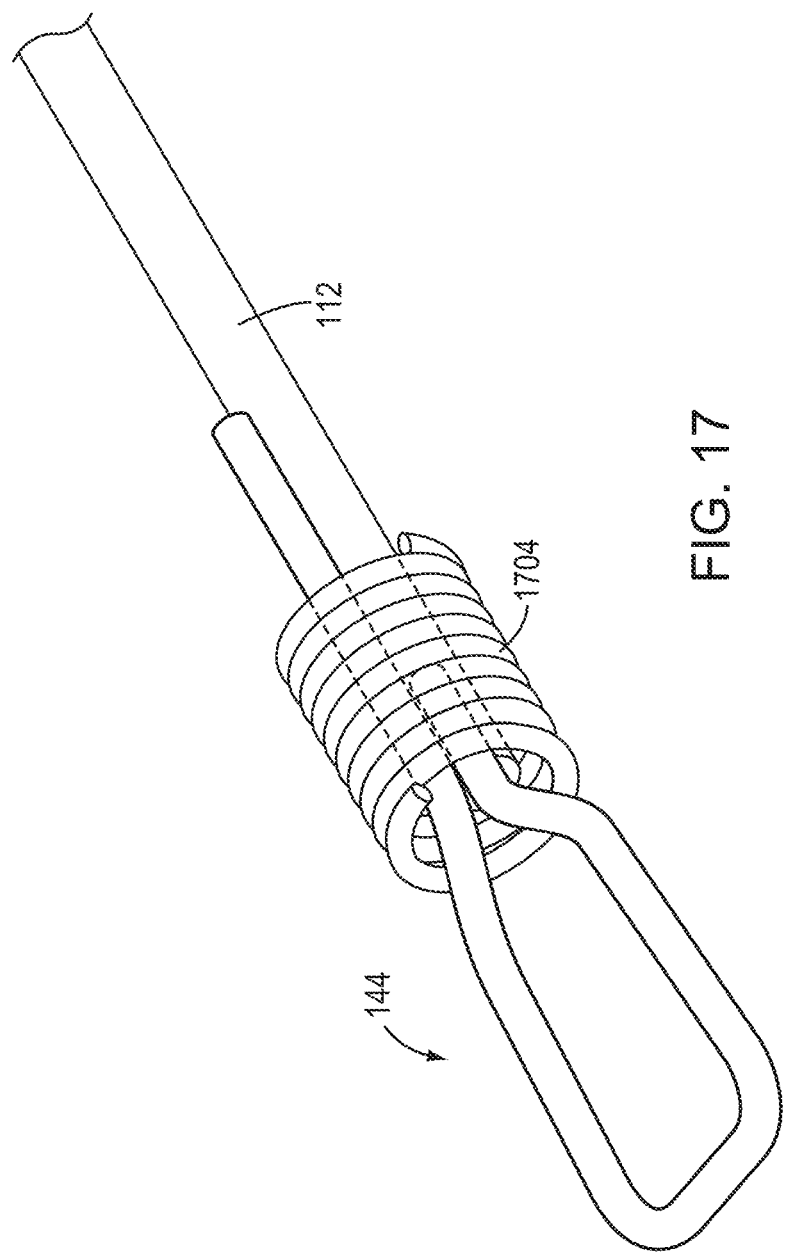

Various configurations of the coil hook 144 are shown in FIGS. 15-17. In particular, FIG. 15 shows a simplified design of a hook 144 that may be used to pull the suture 708 through the blade 124 for detachment. This hook 144 is created by bending the ground core wire (i.e., the tip of the retractable release wire 112) into a hook shape and securing the wire 112 to itself by means of, for example, soldering, welding, and/or adhesive. In some embodiments, bending this core wire in this manner also requires annealing or heat treatment to properly form the hook shape. The advantage of this design is that the dimensional profile of the hook 144 is smaller than if there were separate coil hook components. Also, since there are fewer components, the manufacturing process is simplified.

FIG. 16 shows a configuration in which the coil hook 144 is created by bending a single strand of wire into a coil shape 1604 and then into a hook shape 1608. The end of the hook 1608 may be tucked inside the coil 1604 between the coil 1604 and the core wire 112, and attached in a manner similar to the previously described preferred configuration.

FIG. 17 shows a combination of the two designs depicted in FIGS. 15 and 16 in which the coil hook 144 is formed as described in FIG. 15, and a coil 1704 is then placed over the ends of the formed core wire 112 to further secure the core wire 112 to itself. The coil 1704 may be attached by, for example, means of soldering, welding, and/or adhesive.

In operation, the micro-coil 104 may be introduced, delivered, positioned, and implanted at the desired site within the vasculature using a micro-catheter. In particular, in treating neurovascular or peripheral vascular conditions requiring embolization, the sites may be first accessed by the micro-catheter, which is a flexible, small diameter catheter (typically with an inside diameter between 0.016" to 0.021"), through an introducer sheath/guiding catheter combination that is placed in the femoral artery or groin area of the patient. The micro-catheter may be guided to the site through the use of guidewires. Guidewires typically comprise long, torqueable proximal wire sections with more flexible distal wire sections designed to be advanced within tortuous vessels. A guidewire is visible using fluoroscopy and is typically used to first access the desired site, thereby allowing the micro-catheter to be advanced over it to the desired site.

In one embodiment, once the desired site has been accessed with the micro-catheter tip, the catheter lumen is cleared by removing the guidewire, and the micro-coil 104 is placed into the proximal open end of the micro-catheter and advanced by its delivery pusher 108 through the micro-catheter. When the micro-coil 104 reaches the distal end of the micro-catheter, it is deployed from the micro-catheter and positioned by the delivery pusher 108 into the vascular site. The user (e.g., a physician) may advance and retract the micro-coil 104 several times to obtain a desirable position of the micro-coil 104 within the lesion. Once the micro-coil 104 is satisfactorily positioned within the lesion, the detachment handle 600 is employed to mechanically release the micro-coil 104 into the lesion, as described above. Then, once detachment of the micro-coil 104 has been confirmed, the detachment handle 600 and delivery pusher 108 are removed from the micro-catheter, and additional micro-coils 104 may be placed in the same manner, as necessary for proper treatment.

In other embodiments, the present invention features an implantable assembly. The implantable assembly includes an implantable device and a polymeric stretch resistant member. The implantable device may, as illustrated in FIGS. 7A-10B, be a coil 104 (e.g., a micro-coil) that includes a proximal end 716 and a distal end 712 and that defines a passageway 720 (see FIGS. 7B and 9B), for example a lumen, extending from the proximal end 716 to the distal end 712. The polymeric stretch resistant member 2900 (see FIG. 29), for example a polypropylene filament, may extend along the passageway 720 and be coupled to the distal end 712 at a junction.

Figure 29:
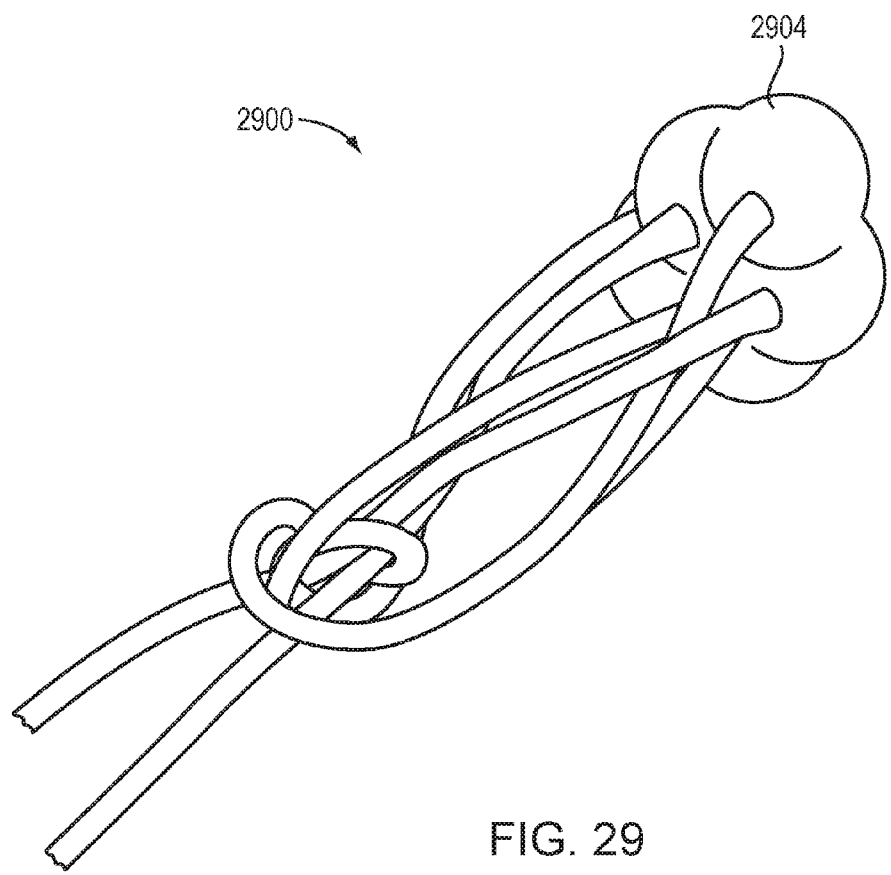
FIG. 29 schematically illustrates a polymeric stretch resistant member in accordance with one embodiment of the invention.

In one embodiment of the present invention, the stretch resistant member 2900 is formed of two components. The first component can be a single, double, or even triple or quadruple stranded stretch resistant material that has a knot formed at a distal end thereof. The second component, which typically is a discrete component (i.e., is different from the first component), may include the same stretch resistant material as the first component and may be knotted around the first component at a point proximal to the knot of the first component. This attachment initially allows the two components to slide relative to one another during the manufacturing process, but that need not be a feature of the final assembly. The second component may include one, two, or more strands of the stretch resistant material, which are pulled toward the distal end of the micro-coil 104 and whose ends may be melted and molded into the winds of the micro-coil 104 to form an atraumatic round tip 2904, such as a tip ball. FIG. 29 depicts an exemplary embodiment of the final system, but without the micro-coil 104 present, so that the detail of the stretch resistant member 2900 is visible.

In one embodiment, and as described in further detail below, the second component of the stretch resistant member includes two strands, and four strand ends (i.e., each end of the two strands) are melted to from the junction (e.g., the tip ball 2904), thereby increasing the overall attachment strength to the melted tip ball 2904. In addition, the length of the strands between the melted tip ball 2904 and the knot-to-knot connection between the two components of the stretch resistant member 2900 prevents the stretch resistant member's first component from being affected by heat during the process of forming the melted tip ball 2904. Advantageously, these features result in the strands of the second component being coupled to the melted tip ball 2904 with a coupling strength greater than a tensile strength of the first component, and thereby avoid a typical failure seen in prior approaches— i.e., a "heat affected" zone of the stretch resistant member (i.e., the portion of the stretch resistant member that enters the melted tip ball) pulling away from and breaking at the melted tip ball when the micro-coil is placed under tension. This tensile failure of prior approaches typically occurs at a tensile load that is significantly lower than the original tensile strength of the stretch resistant member, presumably due to an effect from the process of forming the melted tip ball.

The knot-to-knot connection between the two components of the stretch resistant member 2900 also allows for four strand ends to transition to a single or double strand of suture, which runs through the entire length of the micro-coil 104, providing the desired feature of stretch resistance. This configuration also allows flexibility in component selection, such that a larger diameter suture may be used for the first component of the stretch resistant member 2900.

In one embodiment, a preferred material for the stretch resistant member 2900 is a monofilament polypropylene suture, in a size of 9-0 (which typically has a diameter between 0.0012" and 0.0017"), but the suture may be smaller or larger and/or made from other polymers in other configurations depending on, for example, the inside diameter of the micro-coil 104 component.

As illustrated in FIGS. 7A-10B, and as described earlier, the micro-coil 104 may include a primary coil that is wound from metallic wire (e.g., Platinum 8% Tungsten) and that is then heat set into a secondary shape, such as a complex "3D" shape suitable for "framing" an aneurysm, such as a cerebral aneurysm, or a simple helical shape suitable for "filling" and/or "finishing".

Figure 30A:
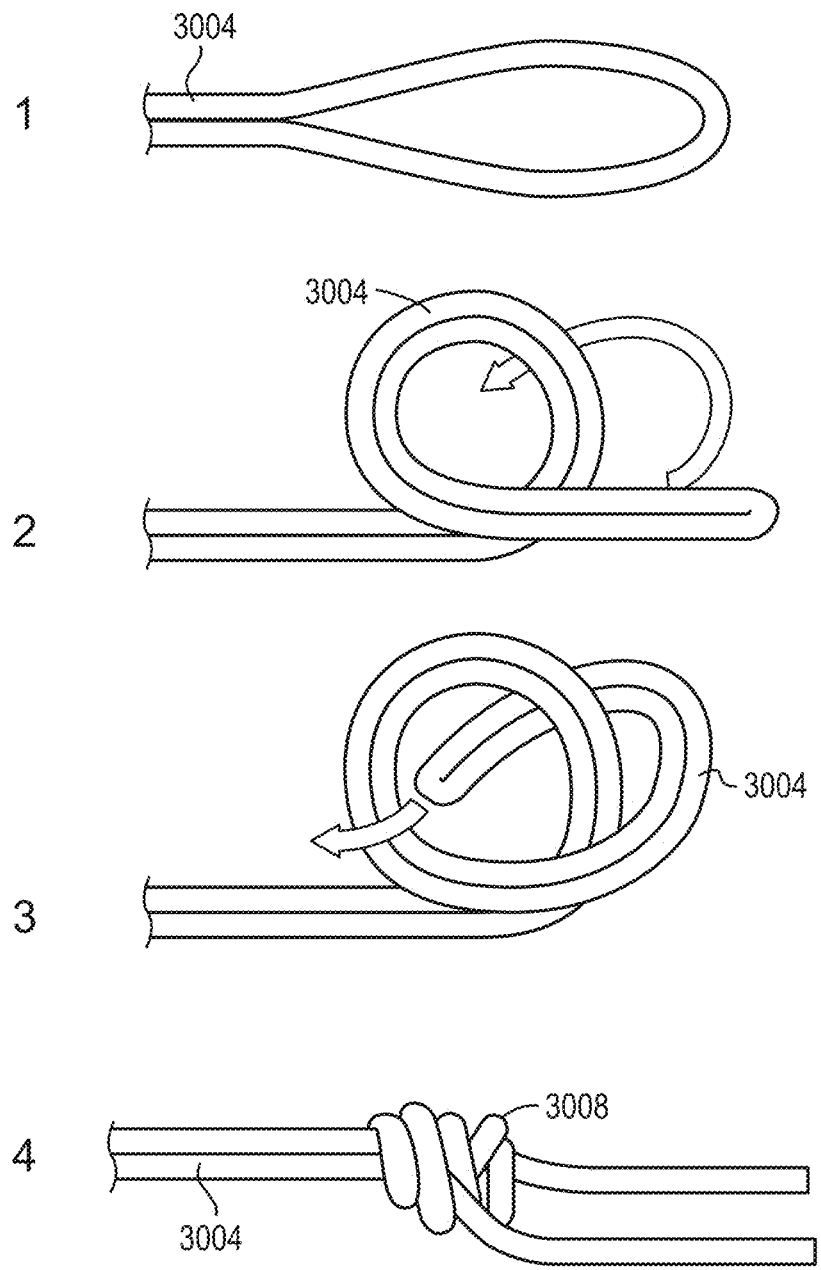
FIGS. 30A-30B schematically illustrate the individual steps in a method of manufacturing an implantable assembly in accordance with one embodiment of the invention.
Figure 30B:
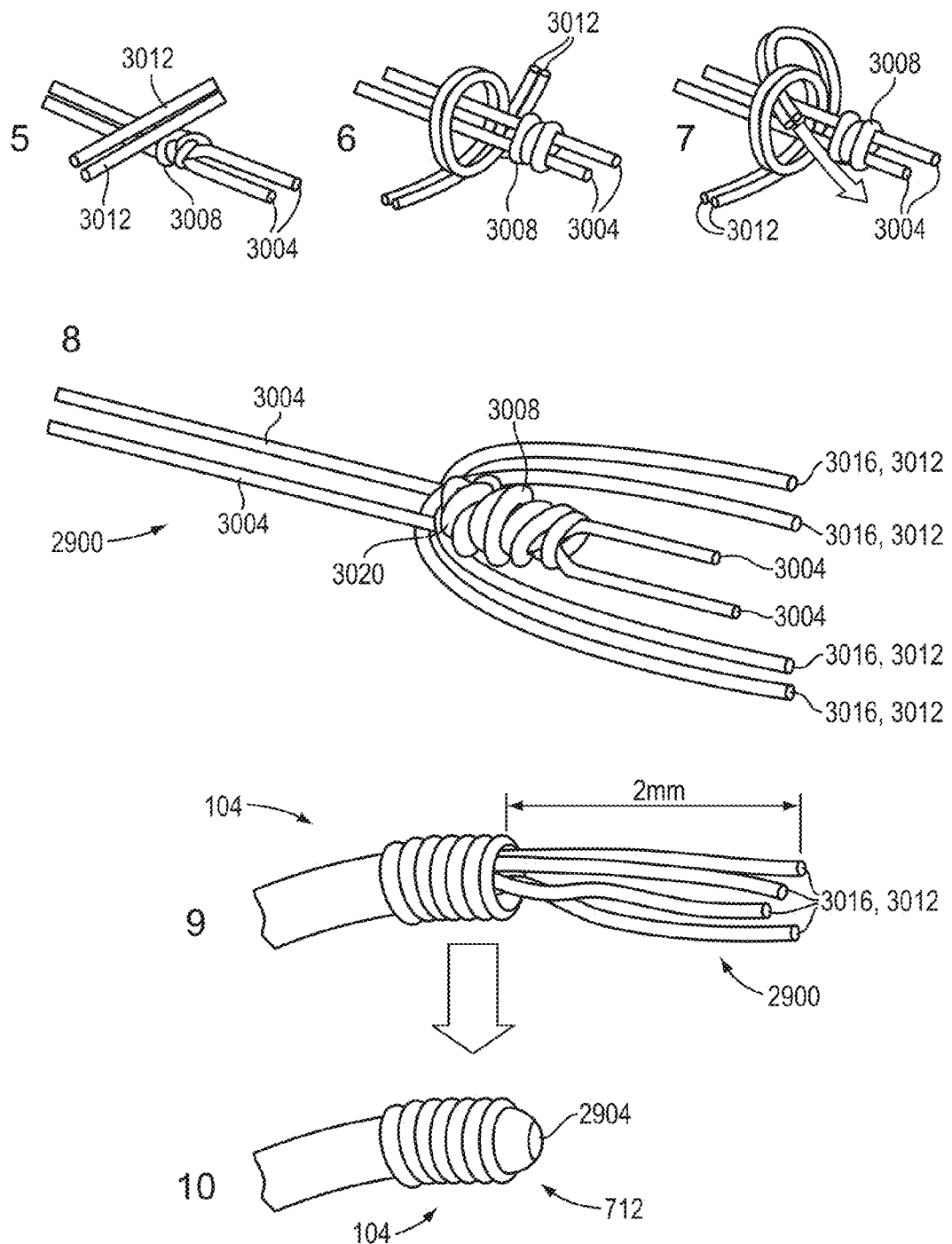

FIGS. 30A-30B depict the individual steps in a method of manufacturing the implantable assembly, according to one exemplary embodiment of the invention. As illustrated, a single strand of suture 3004 (i.e., the first component 3004 of the stretch resistant member 2900) is first looped (Step 1), and an end of the loop is then routed to form a knot 3008 near the end of the loop (Step 2, 3 and 4), which may optionally be cut or cut off at this point. Next, two separate strands 3012 of suture of substantially equal length (i.e., the second component 3012 of the stretch resistant member 2900) are knotted around a proximal end of the first suture 3004 (Steps 5, 6 and 7) such that approximately equal lengths of the suture ends 3016 remain on either side. The ends 3016 of the second suture strands 3012 are then pulled such that the second knot 3020 is tight around the first suture component 3004 and against the knot 3008 of the first component 3004, and then the second suture strands 3012 are pulled toward the distal end of the subassembly 2900, past the knot 3008 of the first component 3004 (Step 8). The loop of the first component 3004 can also be cut or trimmed to a desired length at this point (Step 8). The second suture ends 3016 are also trimmed to a certain suture length (e.g., to a length of 2 mm) and the subassembly 2900 is then inserted into the micro-coil 104 (Step 9). Finally, the second suture ends 3016 are melted, typically through a conductive source such as a soldering iron or a heated rod, and molded into the winds of the micro-coil 104 to form an atraumatic tip 2904 (e.g., a round tip ball 2904) at the distal end 712 of the micro-coil 104 (Step 10). In one particular embodiment, the stretch resistant member 2900 is, as described, coupled to the micro-coil 104 at only the distal end 712 thereof.

In practice, the tensile strength of the stretch resistant member's first component 3004 may be in a range of about 60,000 pounds per square inch (psi) to about 90,000 psi and, by employing the afore-described assembly, the strands of the stretch resistant member's second component 3012 may be coupled to the distal end 712 of the micro-coil 104 at a junction 2904 and with a coupling strength greater than that tensile strength of the first component 3004, for example in a range of about 120,000 psi to about 150,000 psi or more.

Having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. An implantable assembly, comprising:
   an implantable device comprising a proximal end and a distal end and defining a passageway extending from the proximal end to the distal end; and
   a stretch resistant member extending along the passageway and coupled to the distal end at a junction, the stretch resistant member comprising (i) a first component comprising a knot at a distal end thereof and (ii) a second component different from and coupled to the first component, the second component comprising a plurality of strands coupled to the junction and with a coupling strength greater than a tensile strength of the first component.

2. The implantable assembly of claim 1, wherein the implantable device comprises a coil.

3. The implantable assembly of claim 1, wherein the stretch resistant member is coupled to the implantable device at only the distal end.

4. The implantable assembly of claim 1, wherein the stretch resistant member is further coupled to a delivery pusher.

5. The implantable assembly of claim 1, wherein the stretch resistant member comprises a polymeric material.

6. The implantable assembly of claim 5, wherein the polymeric material comprises polypropylene.

7. The implantable assembly of claim 1, wherein the second component is knotted around
   the first component at a point proximal to the knot of the first component.

8. The implantable assembly of claim 7, wherein the plurality of strands of the second component extend from the point proximal to the knot of the first component toward the distal end of the implantable device.

9. The implantable assembly of claim 8, wherein the second component comprises four strand ends that extend from the point proximal to the knot of the first component toward the distal end of the implantable device.

10. The implantable assembly of claim 1, wherein the plurality of strands of the second component are molded to the distal end to form the junction.

11. The implantable assembly of claim 1, wherein the junction comprises an atraumatic tip.

12. The implantable assembly of claim 1, wherein the junction comprises a tip ball.

13. A method of manufacturing an implantable assembly, the method comprising the steps of:
    coupling a first component of a stretch resistant member to a second component of the stretch resistant member, the first and second components being different from one another, the second component comprising a plurality of strands, and the step of coupling the first component to the second component comprising forming a knot at a distal end of the first component;
    extending the stretch resistant member through a passageway defined by an implantable device, the implantable device comprising a proximal end and a distal end; and
    coupling the plurality of strands of the second component to the distal end at a junction and with a coupling strength greater than a tensile strength of the first component.

14. The method of claim 13, wherein the implantable device comprises a coil.

15. The method of claim 13, wherein the stretch resistant member comprises a polymeric material.

16. The method of claim 15, wherein the polymeric material comprises polypropylene.

17. The method of claim 13, wherein coupling the first component to the second component further comprises knotting the second component around the first component at a point proximal to the knot of the first component.

18. The method of claim 17 further comprising extending the plurality of strands of the second component from the point proximal to the knot of the first component toward the distal end of the implantable device.

19. The method of claim 18, wherein the second component comprises four strand ends that are extended from the point proximal to the knot of the first component toward the distal end of the implantable device.

20. The method of claim 13, wherein coupling the plurality of strands of the second component comprises melting distal ends of the plurality of strands.

21. The method of claim 20, wherein coupling the plurality of strands of the second component further comprises molding the melted distal ends of the plurality of strands to the distal end of the implantable device to form the junction.

22. The method of claim 13, wherein the junction comprises an atraumatic tip.

23. The method of claim 13, wherein the junction comprises a tip ball.

24. The method of claim 13 further comprising coupling the stretch resistant member to a delivery pusher.

* * * * *